(12) United States Patent
Buschmann et al.

(10) Patent No.: US 11,795,615 B2
(45) Date of Patent: Oct. 24, 2023

(54) METHODS OF PULP FIBER TREATMENT

(71) Applicant: Clean Chemistry, Inc., Boulder, CO (US)

(72) Inventors: Wayne E. Buschmann, Boulder, CO (US); Damon C. Waters, Boulder, CO (US)

(73) Assignee: Clean Chemistry, Inc., Boulder, CO (US)

( * ) Notice: Subject to any disclaimer, the term of this patent is extended or adjusted under 35 U.S.C. 154(b) by 51 days.

(21) Appl. No.: 17/461,389

(22) Filed: Aug. 30, 2021

(65) Prior Publication Data

US 2021/0388561 A1 Dec. 16, 2021

Related U.S. Application Data

(63) Continuation of application No. 16/148,222, filed on Oct. 1, 2018, now Pat. No. 11,111,629, which is a
(Continued)

(51) Int. Cl.
*D21C 9/16* (2006.01)
*D21C 9/10* (2006.01)
(Continued)

(52) U.S. Cl.
CPC ............ *D21C 9/166* (2013.01); *C02F 1/722* (2013.01); *C02F 9/00* (2013.01); *C12P 3/00* (2013.01);
(Continued)

(58) Field of Classification Search
CPC .............................. D21C 9/166; D21C 9/1068
See application file for complete search history.

(56) References Cited

U.S. PATENT DOCUMENTS 3,719,552 A 3/1973 Farley
3,925,234 A 12/1975 Hachmann et al.
(Continued)

FOREIGN PATENT DOCUMENTS

CN 1142555 A 2/1997
CN 102007230 A 4/2011
(Continued)

OTHER PUBLICATIONS

Gullichsen editor, Chemical Pulping 6A, 1999, Fapet Oy, A137-A145. (Year: 1999).*
(Continued)

*Primary Examiner* — Anthony Calandra
(74) *Attorney, Agent, or Firm* — Holzer Patel Drennan

(57) ABSTRACT

In some embodiments, a method may include treating pulp in pulp and paper mills. The methods may include providing a peracetate oxidant solution and generating a reactive oxygen species. The peracetate solution may include peracetate anions and a peracid. In some embodiments, the peracetate solution may include a pH from about pH 10 to about pH 12. In some embodiments, the peracetate solution has a molar ratio of peracetate anions to peracid ranging from about 60:1 to about 6000:1. In some embodiments, the peracetate solution has a molar ratio of peracetate to hydrogen peroxide of greater than about 16:1. The peracetate oxidant solution may provide enhanced treatment methods of bleaching, brightening, and delignifying pulp fibers involving the use of peracetate oxidant solutions.

13 Claims, 8 Drawing Sheets

Related U.S. Application Data continuation of application No. 15/371,872, filed on Dec. 7, 2016, now abandoned.

(60) Provisional application No. 62/263,900, filed on Dec. 7, 2015.

(51) Int. Cl.

| | | |
|---|---|---|
| *D21C 9/147* | (2006.01) | |
| *C02F 1/72* | (2023.01) | |
| *C02F 9/00* | (2023.01) | |
| *C12P 3/00* | (2006.01) | |
| *C02F 1/76* | (2023.01) | |
| *C02F 103/28* | (2006.01) | |
| *C02F 103/32* | (2006.01) | |
| *C02F 1/00* | (2023.01) | |
| *C02F 1/02* | (2023.01) | |
| *C02F 1/50* | (2023.01) | |
| *C02F 103/00* | (2006.01) | |
| *C02F 103/02* | (2006.01) | |

(52) U.S. Cl.
CPC .......... *D21C 9/1063* (2013.01); *D21C 9/147* (2013.01); *C02F 1/008* (2013.01); *C02F 1/02* (2013.01); *C02F 1/50* (2013.01); *C02F 1/76* (2013.01); *C02F 1/766* (2013.01); *C02F 2103/007* (2013.01); *C02F 2103/023* (2013.01); *C02F 2103/28* (2013.01); *C02F 2103/32* (2013.01); *C02F 2209/04* (2013.01); *C02F 2209/36* (2013.01); *C02F 2303/02* (2013.01); *C02F 2303/04* (2013.01); *C02F 2303/08* (2013.01); *C02F 2303/20* (2013.01)

(56) References Cited

U.S. PATENT DOCUMENTS

| | | |
|---|---|---|
| 4,055,505 A | 10/1977 | Gray |
| 4,076,621 A | 2/1978 | Hardison |
| 4,348,256 A | 9/1982 | Bergstrom et al. |
| 4,393,037 A | 7/1983 | Delaney |
| 4,576,609 A | 3/1986 | Hageman |
| 4,673,473 A | 6/1987 | Ang |
| 4,722,773 A | 2/1988 | Plowman et al. |
| 4,872,953 A | 10/1989 | Smith |
| 4,952,276 A | 8/1990 | Gidlund |
| 4,966,706 A | 10/1990 | Gregor |
| 5,053,142 A | 10/1991 | Sorensen et al. |
| 5,246,543 A | 9/1993 | Meier et al. |
| 5,387,317 A | 2/1995 | Parthasarathy et al. |
| 5,424,032 A | 6/1995 | Christensen et al. |
| 5,431,781 A | 7/1995 | Walsh |
| 5,472,619 A | 12/1995 | Holzhauer et al. |
| 5,494,588 A | 2/1996 | LaZonby |
| 5,565,073 A | 10/1996 | Fraser et al. |
| 5,624,575 A | 4/1997 | Meade et al. |
| 5,683,724 A | 11/1997 | Hei et al. |
| 5,770,035 A | 6/1998 | Faita |
| 5,785,812 A | 7/1998 | Linsten et al. |
| 5,817,240 A | 10/1998 | Miller et al. |
| 6,007,678 A | 12/1999 | Linsten et al. |
| 6,015,536 A | 1/2000 | Lokkesmoe et al. |
| 6,126,782 A | 10/2000 | Liden et al. |
| 6,183,623 B1 | 2/2001 | Cisar et al. |
| 6,258,207 B1 | 7/2001 | Pan |
| 6,294,047 B1 | 9/2001 | Chakar et al. |
| 6,387,238 B1 | 5/2002 | Merk et al. |
| 6,569,285 B1 | 5/2003 | Withenshaw et al. |
| 6,712,949 B2 | 3/2004 | Gopal |
| 8,318,972 B2 | 11/2012 | Buschmann et al. |
| 9,517,955 B2 | 12/2016 | Buschmann |
| 9,517,956 B2 | 12/2016 | Buschmann |
| 9,551,076 B2 | 1/2017 | Buschmann |
| 10,259,729 B2 | 4/2019 | Buschmann |
| 10,472,265 B2 | 11/2019 | Buschmann |
| 10,501,346 B2 | 12/2019 | Buschmann |
| 10,577,698 B2 | 3/2020 | Buschmann |
| 10,611,656 B2 | 4/2020 | Buschmann |
| 10,875,798 B2 | 12/2020 | Buschmann |
| 10,875,799 B2 | 12/2020 | Buschmann |
| 10,883,224 B2 | 1/2021 | Buschmann |
| 10,941,063 B2 | 3/2021 | Buschmann |
| 11,001,864 B1 | 5/2021 | Buschmann |
| 11,111,629 B2 | 9/2021 | Buschmann et al. |
| 2001/0050234 A1 | 12/2001 | Shiepe |
| 2002/0153262 A1 | 10/2002 | Uno et al. |
| 2003/0019757 A1 | 1/2003 | Vetrovec |
| 2003/0019758 A1 | 1/2003 | Gopal |
| 2003/0024054 A1 | 2/2003 | Burns |
| 2004/0035803 A1 | 2/2004 | Cronan et al. |
| 2004/0112555 A1 | 6/2004 | Tolan et al. |
| 2004/0134857 A1 | 7/2004 | Huling et al. |
| 2004/0200588 A1 | 10/2004 | Walker |
| 2005/0183949 A1 | 8/2005 | Daly |
| 2006/0207734 A1 | 9/2006 | Day |
| 2007/0074975 A1 | 4/2007 | Buschmann et al. |
| 2007/0212594 A1 | 9/2007 | Takasu et al. |
| 2007/0243449 A1 | 10/2007 | Sotomura et al. |
| 2009/0012346 A1 | 1/2009 | Al Nashef et al. |
| 2009/0090478 A1 | 4/2009 | Hollomon et al. |
| 2009/0152123 A1 | 6/2009 | Butler et al. |
| 2009/0285738 A1 | 11/2009 | Winter et al. |
| 2009/0314652 A1 | 12/2009 | Buschmann |
| 2010/0078331 A1 | 4/2010 | Scherson et al. |
| 2010/0160449 A1 | 6/2010 | Rovison, Jr. et al. |
| 2010/0176066 A1 | 7/2010 | Budde et al. |
| 2010/0179368 A1 | 7/2010 | Conrad |
| 2010/0320156 A1 | 12/2010 | Olaiya et al. |
| 2011/0017066 A1 | 1/2011 | Takeuchi et al. |
| 2011/0024361 A1 | 2/2011 | Schwartzel |
| 2011/0123642 A1 | 5/2011 | Wilmotte |
| 2011/0232853 A1 | 9/2011 | Yin |
| 2012/0067532 A1 | 3/2012 | Lee |
| 2012/0091069 A1 | 4/2012 | Fischmann |
| 2012/0108878 A1 | 5/2012 | Conrad |
| 2012/0145643 A1 | 6/2012 | Pandya |
| 2012/0240647 A1 | 9/2012 | Montemurro |
| 2012/0267315 A1 | 10/2012 | Soane et al. |
| 2012/0322873 A1 | 12/2012 | Atkins et al. |
| 2013/0259743 A1 | 10/2013 | Keasler et al. |
| 2013/0264293 A1 | 10/2013 | Keasler et al. |
| 2014/0069821 A1 | 3/2014 | Marcin et al. |
| 2014/0072653 A1 | 3/2014 | Buschmann |
| 2014/0131217 A1 | 5/2014 | Buschmann |
| 2014/0131259 A1 | 5/2014 | Goldblatt |
| 2014/0197102 A1 | 7/2014 | Van Der Wal et al. |
| 2014/0205777 A1 | 7/2014 | Hawkins et al. |
| 2014/0238626 A1 | 8/2014 | Tsuji et al. |
| 2014/0374104 A1 | 12/2014 | Seth |
| 2016/0068417 A1 | 3/2016 | Buschmann |
| 2016/0297697 A1 | 10/2016 | Buschmann |
| 2016/0318778 A1 | 11/2016 | Buschmann |
| 2017/0051417 A1 | 2/2017 | Buschmann |
| 2017/0107128 A1 | 4/2017 | Buschmann |
| 2017/0114468 A1 | 4/2017 | Buschmann |
| 2017/0158537 A1 | 6/2017 | Buschmann |
| 2017/0159237 A1 | 6/2017 | Buschmann |
| 2017/0335515 A1 | 11/2017 | Buschmann |
| 2018/0023250 A1 | 1/2018 | Buschmann |

FOREIGN PATENT DOCUMENTS

| | | |
|---|---|---|
| EP | 0480469 A3 | 4/1992 |
| FR | 2776312 A1 | 9/1999 |
| WO | 9402423 A1 | 2/1994 |
| WO | 9412721 A1 | 6/1994 |
| WO | 9739179 A1 | 10/1997 |
| WO | 1999032710 A1 | 7/1999 |
| WO | 2000069778 A1 | 11/2000 |
| WO | 2008056025 A2 | 5/2008 |
| WO | 2010059459 A1 | 5/2010 |
| WO | 2012166997 A3 | 12/2012 |

(56) References Cited

FOREIGN PATENT DOCUMENTS

| | | |
|---|---|---|
| WO | 2013060700 A1 | 5/2013 |
| WO | 2013064484 A1 | 5/2013 |
| WO | 2014039929 A1 | 3/2014 |
| WO | 2014100828 A1 | 6/2014 |
| WO | 2016037149 A1 | 3/2016 |
| WO | 2016154531 A1 | 9/2016 |
| WO | 2017100284 A1 | 6/2017 |
| WO | 2017100299 A1 | 6/2017 |
| WO | 2018106285 A1 | 6/2018 |

OTHER PUBLICATIONS

Coyle et al.; "Peracetic Acid as an Alternative Disinfection Technology for Wet Weather Flows"; Water Environment Research; Aug. 2014; pp. 687-697.

Gullichsen et al., eds.; Chemical Pulping; Papermaking Science and Technology; Book 6A; 1999; Fapet Oy; pp. A40-A41 and A616-A665.

Hill et al.; "Part 1: Peracetic Acid—An effective alternative for Chlorine compound Free Delignification of Kraft Pulp"; 1992; Pulping Conference; pp. 1219-1230.

Pedros et al.; "Chlorophyll fluorescence emission spectrum inside a leaf"; The Royal Society of Chemistry and Owner Societies; 2008; No. 7; pp. 498-502.

Shackford; "A Comparison of Pulping and Bleaching of Kraft Softwood and Eucalyptus Pulps"; 36th Intl. Pulp and Paper Congress and Exhibition; Oct. 13-16, 2003; Sao Paulo, Brazil; 17 pgs.

Smook, Handbook for Pulp & Paper Technologists, 1992, Chapter 14: Secondary Fiber; Fifth printing 2001, Angus Wilde Publications, Vancouver B.C., pp. 209-219.

Smook, Handbook for Pulp & Paper Technologists, 1992, Chapter 4: Overview of Pulping Methodology and Chapter 7: Kraft Pulping, Fifth printing 2001, Angus Wilde Publications, Vancouver B.C., pp. 36-44 and 74-83.

Suihko et al.; "A study of the microflora of some recycled fibre pulps, boards and kitchen rolls"; The Journal of Applied Microbiology; 1997; vol. 83; pp. 199-207.

Suslow; "Oxidation-Reduction Potential (ORP) for Water Disinfection Monitoring, Control, and Documentation"; Univ. California; Division of Agriculture and Natural Resources; ANR Publication 8149; 5 pgs.; http://anrcatalog.ucdavis.edu; 2004; 5 pgs.

Szabo et al.; "Utilization of NaClO and $H_2O_2$ as a Source of The Singlet Oxygen for The Environmental Bleaching of Pulp"; Cellulose Chem. Technol.; vol. 28; 1994; pp. 183-194.

Verween et al.; "Comparative toxicity of chlorine and peracetic acid in the biofouling control of Mytilopsis leucophaeata and Dreissena polymorpha embryos (Mollusca, Bivalvia)"; International Biodeterioration & Biodegradation; vol. 63, No. 4; 2009; pp. 523-528.

Xu et al.; "Isotope and surface preparation effects on alkaline dioxygen reduction at carbon electrodes"; J. Electrochemical Chemistry 410; 1996; pp. 235-242.

\* cited by examiner

METHODS OF PULP FIBER TREATMENT

RELATED APPLICATIONS

This application is a continuation of U.S. patent application Ser. No. 16/148,222 entitled "METHODS OF PULP FIBER TREATMENT" filed Oct. 1, 2018, which is a continuation of U.S. patent application Ser. No. 15/371,872 entitled "METHODS OF PULP FIBER TREATMENT" filed Dec. 7, 2016, which claims priority to U.S. Provisional Patent Application No. 62/263,900 entitled "METHODS OF MICROBIAL CONTROL" filed on Dec. 7, 2015, the entire contents of each of which are incorporated herein by reference.

BACKGROUND OF THE INVENTION

1. Field of the Invention

The present disclosure generally relates to pulp fiber treatment using peracetate oxidant solutions. The disclosure more particularly relates to methods of bleaching, brightening, and delignifying pulp fibers involving the use of peracetate oxidant solutions.

2. Description of the Relevant Art

A variety of methods have been developed for delignification of wood pulp fibers after the initial pulping to achieve brighter unbleached grades and bleachable grades (e.g., kappa number 10-15). Common delignification methods include reductive methods (e.g., extended or enhanced sulfide digestion), oxidative methods (e.g., oxygen delignification, alkaline hydrogen peroxide extraction and combinations), and enzymatic methods (e.g., zylanase).

Bleaching of pulp (wood and non-wood fibers) is commonly done by elemental chlorine free (ECF) processes and totally chlorine free (TCF) processes. The ECF processes are currently more economic and common than TCF in large pulp and paper mills for reaching white fiber grades of greater than about 80% ISO brightness. ECF bleaching commonly involves several chlorine dioxide stages with washing and extraction stages in between. TCF processes may incorporate extended delignification stages and alternative bleaching chemicals including multiple alkaline hydrogen peroxide stages, ozone and peracetic acid to achieve brighter fiber grades.

Singlet oxygen is well suited for oxidation of phenols, chlorinated phenols and similar electron-rich phenolic materials including lignin. Lignin generally consists of cross-linked polyphenolic materials created by enzyme-mediated polymerization of coniferyl, sinapyl and p-coumaryl alcohols. Singlet oxygen (which is not a radical) is relatively selective towards phenol oxidation and has little direct impact on cellulose fibers. In contrast, ozone and radicals including elemental chlorine, hydroxyl radical, hydroperoxyl radical, superoxide and even triplet oxygen are more reactive towards cellulose in conventional delignification and bleaching processes.

The selectivity of singlet oxygen towards the oxidation and break down of lignin and non-cellulose materials avoids non-selective reactions that break down cellulose by radical-based or radical-forming oxidants including gaseous chlorine, chlorine dioxide and ozone. Reactive oxygen radical species such as superoxide and peroxyl radicals are known to form during higher pressure and temperature oxygen delignification processes and can cause damage to cellulose fibers. It is generally known in the art that cellulose fibers are susceptible to damage by radical species, which reduces fiber yield and fiber strength. The addition of alkali to oxygen delignification and hydrogen peroxide extraction is common practice to increase the oxidation and extraction rates of lignin from cellulose fiber. However, excessive alkali concentrations or exposure times will also cause damage to cellulose fiber.

The rate of delignification also impacts the preservation of pulp fiber yield, strength and quality. Shorter exposure time of fiber to oxidizing and alkaline conditions may reduce the amount of non-selective breakdown of cellulose fiber. For example, an oxygen delignification process for wood pulp is typically 30 to 60 minutes retention time to achieve about 20-60% kappa reduction depending on the oxygen stage design, operating conditions and wood species. In comparison, the use of the peracetate oxidant formulation may achieve the same kappa reduction performance in 1 to 20 minutes contact time or retention time depending on the wood species, process design and operating conditions. Shorter retention times may also increase pulp throughput or decrease the size and cost of equipment for a delignification process.

Studies of singlet oxygen oxidation of phenols has historically been conducted using photocatalytic methods to generate singlet oxygen in-situ. This method often involves irradiation of a solution containing a photosensitive dye (e.g., rose bengal, methylene blue) which transfers its photo-excited state energy to dissolved oxygen. Relying on a dye mediated photooxidation process is not practical for pulp delignification due to optically opaque pulp mixtures and the rapid breakdown of photosensitive dyes by singlet oxygen and other ROS.

Polychlorinated phenols are one of the major absorbable organic halogens (AOX) that may be discharged in pulp bleaching effluents. Dioxins, furans and other halogenated organic materials are also formed during chlorine and chlorine dioxide bleaching and are included in the AOX category. AOX formation is highly dependent on the lignin content (proportional to kappa number) of the pulp prior to bleaching. The more reduction in kappa number prior to bleaching the less AOX formation potential. The ROS-generating peracetate formulation has the ability to reduce kappa number (lignin content) significantly.

Furthermore, there are few economically viable options for delignification of wood and non-wood pulps on smaller scales than those feasible for traditional pulp and kraft pulp mills. Oxygen delignification has very high capital costs and significant operating and maintenance costs. Digesters for reductive, hydrolytic and enzymatic methods have moderate capital costs but may occupy a large footprint and have long retention times. Options for delignification that are lower cost and simpler to implement or retro-fit into a pulp treatment process will be beneficial to smaller and existing fiber lines.

Fiber products, including fiber board and molded fiber products, produced from pulps of various types used in food packaging and compostables are generally unbleached if gaseous chlorine, chlorine bleach and chlorine dioxide are excluded from the processing. Producing these products with brightened (e.g., 65% ISO brightness or greater) or near-white grades of fiber without the use of traditional bleaching lines is desirable. Using the peracetate oxidant technology can readily provide a rapid brightening stage over a wide range of production capacity and can be implemented rapidly with minimal capital outlay and space requirements. For existing pulp and paper mills the peracetate oxidant technology is a relatively simple, safe and low-cost retrofit or drop-in replacement. The byproducts of the peracetate oxidant formulation do not contain chlorides and are compatible with the recovery boiler in a closed-cycle mill process.

Using the peracetate oxidant formulation is significantly safer than chlorine and chlorine dioxide. Peracetate oxidant solutions are composed of sodium peracetate salt, which is a water soluble solid in its native form. Salts in general have significantly lower vapor pressures than liquids and gases at room temperature. A small fraction of the sodium peracetate can be present as peracetic acid, however, peracetic acid is consumed by reactions with sodium peracetate and does not reach significant concentrations in solution. Exposure to sodium peracetate solution is limited to inhalation of an aerosol or mist and exposure to liquid concentrates.

For comparison, a 5% peracetic acid solution has a reported vapor pressure of 22 mm Hg (0.029 atm). Peracetic acid is a liquid in its native form with a boiling point of 25° C. The 8 hour time weighted average acute exposure guidelines (TWA-AEGL) in air are currently 0.52 mg/m$^3$ (level 1), 1.6 mg/m$^3$ (level 2) and 4.1 mg/m$^3$ (level 3).

Chlorine dioxide is a gas with a vapor pressure of greater than 1 atm and limited water solubility. Chlorine dioxide's solubility limit in water is 0.8% wt/vol at 20° C., but rapidly off-gasses above 0.3%. The 8 h TWA permissible exposure limit (PEL) in air is currently 0.3 mg/m$^3$. The immediately dangerous to life or health (IDLH) concentration is 13.8 mg/m$^3$ and exposure to greater than 1187 mg/m$^3$ (430 ppm) can cause death within 30 minutes.

The use of elevated concentrations of chlorine dioxide in water treatment is particularly hazardous. For example, the head space of a tank containing water with 20 mg/L chlorine dioxide will slowly equilibrate to a head space concentration of 807 mg/m$^3$ at 25° C. and 1 atm according to Henry's law calculations. Pulp bleaching operations using chlorine dioxide at several hundred to several thousand mg/L concentrations and elevated temperatures pose severe exposure hazards over large areas if not properly contained. Gases are more difficult to contain than liquid solutions with low vapor pressures. Chlorine dioxide is also an explosive gas and can undergo explosive decomposition above 10% v/v chlorine dioxide in air. Above 14% explosions are violent. Explosive vapor concentrations can be achieved in pipes that are only partially filled with moderately concentrated chlorine dioxide solutions.

Water used in chlorine and chlorine dioxide bleaching stages is not compatible with recovery boilers and other process equipment outside of the bleaching circuit due to the highly corrosive chloride and chlorate content. Chlorides would accumulate in closed loop processes in a pulp mill used upstream of the bleaching circuit causing corrosion damage to conventional process equipment. Therefore, the water from bleaching stages, which also contains the majority of AOX emissions, must be segregated, treated and disposed of as waste water. The peracetate oxidant formulation contains no chloride content and its organic carbon content can be combusted in the recovery boilers. Each chlorine or chlorine dioxide bleaching stage that is replaced or reduced by using the peracetate oxidant formulation upstream of the bleaching circuit represents a reduction in the waste water stream, reduction in AOX and reduced financial and environmental costs of treatment and disposal or discharge.

Corrosivity of radical compounds used in the delignification, brightening and bleaching stages is another issue, especially when these compounds come in contact with various process materials such as steel, copper and brass alloys. These compounds used in processes where elevated temperatures and turbulence are present in the liquid phase should ideally have low vapor pressures to minimize vapor phase corrosion of surrounding equipment and structures. Compounds that are gases in their native form are the most volatile and present the greatest corrosion and occupational exposure hazards, including chlorine, chlorine dioxide and ozone.

Microbial control in water is imperative to a wide variety of processing and manufacturing systems. These systems can include water recycling loops, pulp and paper mills, feedstock slurry, water loops, feedstock processing systems, and non-potable water systems. Treatment of water for microbial control in water recycle loops is critical for maintaining efficient processes, protecting equipment from biofouling and biocorrosion, preventing contamination of products, reducing downtime and protecting the health of people exposed to such processes and products. Furthermore, microbial control in water recycle loops also provides odor control by minimizing fermentation, hydrogen sulfide production and algal decomposition.

Microbial control in pulp and paper mills serves to protect the integrity of pulp slurries, coating ingredients, whitewater loop, process equipment, and paper quality. Controlling sessile bacteria helps to prevent the accumulation of biofilm deposits which cause microbiologically influenced corrosion (i.e., biocorrosion). Slime deposits are often a combination of bacteria and fungi. Importantly, when biofilms and their detritus detach from surfaces in the wet end papermaking process, they can cause holes and other defects in finished paper products. Therefore, preventing biofilm growth helps to avoid such defects.

Microbial control may also occur on surfaces serving to bleach, sanitize and/or disinfect the surfaces of a processing or manufacturing system.

Microbial control targets include aerobic and anaerobic bacteria (slime formers, acid producers, metal depositors, nitrobacteria, sulfate reducers, nitrate reducers), fungi, algae, molds, spores and yeast. Some bacteria are pathogenic, for example, *Legionella pneumophila*, which poses health risks. Some algae, such as cyanobacteria, produce algal toxins that pose potential health hazards.

Compounds used for microbial control need to be effective and efficient at neutral and alkaline pH. They also need to be effective at elevated levels of suspended solids (including silt, pulp, fillers, pigments, suspended metals, oils, polymers) and dissolved solids (including salt, scaling minerals, carbonate, dissolved metals, scale inhibitors and other additives that may be encountered in various processes).

Microbial control is generally achieved using chemical biocides. Oxidizing biocides (e.g., chlorine gas, chlorine bleach, iodine, hypobromous acid, chlorine dioxide, chloramines, bromamines, fluorine, peroxyacetic acid, hydrogen peroxide, ozone) are typically fast acting and relatively short lived compared to non-oxidizing biocides (e.g., glutaraldehyde, dodecylguanidine, bromohydroxyacetophenone, bronopol, hydantoins, isothiazolins), which are slower acting, but leave long lasting active residuals that can persist for several weeks in the environment. Commonly used oxidizing biocides are effective in the treatment of water with relatively low levels of contaminants, however significant issues arise when higher concentrations of organic materials and salinity are present. Microbial resistance to chlorine and bromine-based oxidizing biocides is a growing issue in municipal and industrial water systems.

There are numerous tradeoffs in selecting a biocide for specific applications. Chlorine was first used in municipal water treatment in the U.S. in 1909 as a disinfectant. Since then chlorine and chlorine-based biocides have been the standard for large scale municipal and industrial disinfection. Oxidizing biocides based on free chlorine and bromine in water react readily with organic materials to form halogenated disinfection byproducts, which are persistent in the environment and often exhibiting high toxicity. The antimicrobial activity of aqueous chlorine and bromine decreases rapidly above about pH 7 and pH 8, respectively. Chlorine dioxide is an effective biocide over a wider pH range and has a lower potential to form halogenated disinfection byproducts if generated properly. However, byproducts of chlorine dioxide include chlorite and chlorate, which are regulated in drinking water. Peroxyacetic acid (PAA), which is a stabilized mixture of PAA, hydrogen peroxide, acetic acid and water, is an effective biocide, but not as efficient as chlorine dioxide in that higher doses are necessary to achieve similar performance. PAA performance declines as pH becomes more alkaline and promotes non-beneficial decomposition reactions between PAA, hydrogen peroxide and metal contaminants. Hydrogen peroxide by itself has significantly lower antimicrobial efficacy than PAA and halogen-based biocides while microbes can rapidly develop tolerance to it in water recycle loops. PAA and hydrogen peroxide rapidly degrade in the environment and form significantly fewer disinfection byproducts than halogenated biocides. Oxidizing biocides can also directly oxidize odor-causing materials such as phenols, sulfides and mercaptans.

Corrosivity of oxidizing biocides is another issue, especially when the biocides come in contact with various process materials such as steel, copper and brass alloys. Oxidizing biocides used in processes where elevated temperatures and turbulence are present in the liquid phase should ideally have low vapor pressures to minimize vapor phase corrosion of surrounding equipment and structures. Biocide materials that are gases in their native form are the most volatile and present the greatest corrosion and occupational exposure hazards, including chlorine, chlorine dioxide and ozone.

Control of biocide dosing in a process stream by monitoring the oxidation potential of the treated water is an advantage for real-time process control. The oxidation-reduction potential (ORP) of a solution can be correlated with a level of biocidal control at a given pH and often with the concentration of active biocide present (and corresponding corrosivity). Various forms of chlorine, bromine, chlorine dioxide and sometimes ozone can provide a strong ORP response when used at low concentrations at neutral to moderately alkaline pH. For example, the ORP of chlorine bleach or chlorine dioxide at a 1-2 ppm concentration in relatively clean fresh water at pH 7 can exceed 700 mV vs standard hydrogen electrode (ORP greater than 650 mV typically provides effective bacteria control). In contrast, PAA, hydrogen peroxide and non-oxidizing biocides do not provide a meaningful ORP response above a dissolved oxygen background in fresh water, which is about 420-520 mV at pH 7.

There is a need for highly effective and fast acting oxidizing biocides that are safer to use, have lower environmental impacts and contribute to pollution prevention efforts. Water-based alkyl peroxide salt solutions that efficiently produce reactive oxygen species (ROS) are a class of highly active oxidants that provide multiple biocidal species, have low volatility, degrade to benign residuals, can be produced from stable feedstocks under mild conditions, and reduce or eliminate several harmful disinfection and oxidation byproducts.

There is a need for improved delignification and extraction of materials from pulp fibers for brightening and bleaching purposes. It is desirable to find an efficient and cost effective method of treating pulp without the use of halogen-containing bleaching chemicals. The reactive oxygen species (ROS) generating peracetate formulation of the present invention may be used for decreasing the use of halogen-containing oxidants and thus TOX and AOX formation. Use of the peracetate formulation in pulp processing may reduce pollution, reduce waste water effluent and enhance processes for extracting lignin from cellulosic fiber for the recovery of lignin from the black liquor or spent oxidant liquor.

SUMMARY OF THE INVENTION

In some embodiments, the ROS-generating peracetate formulation of the present invention may be used for delignification and extraction of materials from pulp fibers for brightening and bleaching purposes. These materials can include but are not limited to: lignin, hexenuronic acid, dihydroconiferyl alcohol, secoiso-lariciresinol, mannans, xylans, hemicellulose, chemical linkages between lignin and carbohydrates (e.g., benzyl ether linkages) and other oxidizable "non-lignin" structures that contribute to kappa number. It may also be used for extracting lignin from cellulosic fibers for the recovery of lignin from the black liquor or spent oxidant liquor.

In some embodiments, the ROS generated by the parent peracetate formulation, particularly singlet oxygen, are the primary chemical species doing the delignification, brightening and bleaching of fibers. The direct reaction of peracetate with pulp is minimal, which contrasts with the use of peracetic acid in combination with hydrogen peroxide as the primary oxidants, which have much lower performance efficiency (and therefore, higher cost) for delignification, brightening and bleaching.

In some embodiments, the peracetate oxidant formulation of this invention produces singlet oxygen as the primary reactive oxidant species and therefore avoids damage of cellulose fibers relative to other chemical methods for delignification and bleaching. The peracetate oxidant formulation also performs well at its natural pH without the use of additional alkali, which also reduces to damage to cellulose fibers. Using the peracetate oxidant formulation to reduce or eliminate the amount of oxygen delignification and/or eliminate at least a portion of pulp bleaching with chlorine, chlorine dioxide or ozone can improve pulp yield, fiber strength, fiber quality and fiber product strength. The peracetate oxidant formulation provides the first known bulk source of singlet oxygen for pulp delignification and bleaching.

In some embodiments pH has a significant impact on the reactivity between singlet oxygen and lignin. Raising the pH close to or above the pKa of the phenolic compound (typically greater than pH 9 and preferably greater than pH 10) significantly accelerates oxidation. [Ref: Nowakowska, M.; Kepczynski, M.; Journal of Photochemistry and Photobiology A: Chemistry; 116 (1998) 251-256.] The oxidation of phenol by singlet oxygen in aqueous alkaline conditions was determined to proceed through a benzoquinone intermediate, which was further oxidized by singlet and triplet oxygen forming byproducts including carbon dioxide, maleic acid and fumaric acid. [Ref: Gerdes, R.; Wohrle, D.;

Spiller, W.; Schneider, G.; Schnurpfeil, G.; Schulz-Ekloff, G.; Journal of Photochemistry and Photobiology A: Chemistry; 111 (1997) 65-74.]

Polychlorinated phenols are one of the major absorbable organic halogens (AOX) that may be discharged in pulp bleaching effluents. Also in the AOX category are dioxins, furans and other halogenated organic materials. AOX formation is highly dependent on the lignin content (proportional to kappa number) of the pulp prior to bleaching. The more reduction in kappa number prior to bleaching the less AOX formation potential. In some embodiments, the ROS-generating peracetate oxidant formulation has the ability to reduce kappa number (lignin content) significantly. For example, the peracetate oxidant formulation can reduce hardwood kappa numbers of 14-20 down to 5-12 in a single treatment stage and can reduce softwood kappa numbers of 30-35 down to 15-25 in a single treatment stage In some embodiments, delignification performance of the ROS-generating peracetate oxidant formulation is high, even at pH 9 or less. Applying the peracetate oxidant in high doses in a single step process is effective, but this approach can be costlier compared to multiple, lower doses of oxidant. The capital cost for the peracetate oxidant technology is almost negligible compared to traditional processes including oxygen delignification and chlorine dioxide bleaching lines. Minimal capital cost may offset the total cost of ownership to use the peracetate oxidant technology in facilities having little to no existing infrastructure for brightening or bleaching of fiber.

In some embodiments, methods to use the ROS-generating peracetate oxidant formulation more efficiently were developed to reduce operating costs of feedstocks so that it can directly compete with chlorine dioxide on a cost basis when considering reducing chlorine chemicals, reducing chlorine bleaching steps, reducing AOX formation and emissions, reducing bleaching effluent for treatment, and reducing capital costs relative to increasing the capacity of conventional mill infrastructure. Additional financial benefits may be realized in lower corrosion-caused maintenance costs, higher pulp yields, greater fiber product strength and increased throughput of an existing pulp line.

Several process variables are important for chemical pulp delignification, brightening and bleaching including chemical concentration, amount of chemical per unit mass of pulp, pulp consistency, temperature, mixing method, mixing energy, contact time with a chemical, residence time in a process stage, number of process stages, process equipment design and overall process design. These variables are incorporated into preferred methods for efficient use of the peracetate oxidant formulation. Methods of using the ROS-generating peracetate oxidant formulation are influenced by the ROS generation behavior of the peracetate oxidant formulation. In some embodiments, thermal acceleration of the reaction(s) that produce ROS, especially singlet oxygen, from the "parent" peracetate formulation is particularly important to performance. In some embodiments increasing the temperature of the peracetate oxidant in pulp treatment accelerates delignification rate by increasing the production rate and concentration of ROS. In some embodiments, increasing the peracetate oxidant concentration in pulp treatment accelerates delignification rate. In some embodiments, increasing pulp consistency increases delignification rate and efficiency by decreasing the dilution of the peracetate oxidant in the liquid phase of the pulp. In some embodiments increasing mixing energy or mixing intensity increases delignification rate.

In some embodiments, heating or thermal acceleration or activation of peracetate oxidant solutions to a temperature between about 50° C. to about 95° C. accelerates the formation of ROS (singlet oxygen) from a "parent" peracetate formulation as shown by enhanced rates of delignification, bleaching and biocidal activity with increasing temperature. Thermal activation that accelerates ROS production rate is useful for pulp treatment in heated environments and hot chemical sanitizing processes.

In some embodiments, the ability to conduct delignification at medium pulp consistency (10-20% oven dried fiber by weight) has a significant impact on economics compared to low pulp consistency (0.1-10% oven dried fiber by weight) processing. At medium consistency, the mixing efficiency and rate of pulp fibers with the peracetate oxidant solution is a critical parameter for maximizing the rate and extent of delignification.

The rate of delignification also impacts the preservation of pulp fiber yield, strength and quality. Shorter exposure of fiber to oxidizing and alkaline conditions may reduce the amount of non-selective breakdown of cellulose fiber. For example, an oxygen delignification process for wood pulp is typically 30 to 60 minutes retention time to achieve about 20-60% kappa reduction depending on the oxygen stage design, operating conditions and wood species. In an embodiment, the use of the peracetate oxidant formulation may achieve the same kappa reduction performance in 1 to 20 minutes contact time or retention time depending on the wood species, process design and operating conditions. Shorter retention times may also increase pulp throughput or decrease the size and cost of equipment for a delignification process.

Fiber products, including fiber board and molded fiber products, produced from pulps of various types used in food packaging and compostables are generally unbleached if chlorine and chlorine dioxide are excluded from the processing. Producing these products with brightened (e.g., 65% ISO brightness or greater) or near-white grades of fiber without the use of traditional bleaching lines is desirable. In some embodiments, using the peracetate oxidant technology can readily provide a rapid brightening stage over a wide range of production capacity and can be implemented rapidly with minimal capital outlay and space requirements. For existing pulp and paper mills the peracetate oxidant technology is a relatively simple, safe and low-cost retrofit or drop-in replacement. The byproducts of the peracetate oxidant formulation do not contain chlorides and are compatible for being sent to the recovery boiler in a closed-cycle mill process.

In an embodiment, a method of using the peracetate oxidant formulation in bleaching sequences. For example, a conventional four-stage bleaching sequence may use the sequential pulp treatment stages of chlorine dioxide ($D_0$), oxidative extraction with alkaline hydrogen peroxide ($E_{OP}$), chlorine dioxide ($D_1$), and chlorine dioxide ($D_2$). This bleaching sequence may be abbreviated as D(EOP)DD. Hydrogen peroxide is used in the sequence to reduce chlorine dioxide use.

In some embodiments, the peracetate oxidant solution may be used prior to the bleaching sequence (allowing its spent liquor to be sent to the recovery boiler) such that at least one of the chlorine dioxide stages, such as $D_2$, may be eliminated. This approach reduces the number of stages needed in a bleach plant, reduces the amount of AOX produced, reduces the amount of chlorinated waste water for disposal and reduces the amount of bleaching chemicals needed. Eliminating one chlorine dioxide stage may increase fiber strength and pulp yield.

In some embodiments, the peracetate oxidant solution may be used within the bleaching sequence as a replacement for the $E_{OP}$ stage. The peracetate oxidant is more effective than hydrogen peroxide for removing or extracting residual lignin and is a more selective oxidant than alkaline hydrogen peroxide. The greater performance and selectivity of the peracetate solution may eliminate at least one chlorine dioxide stage, such as eliminating $D_2$ or eliminating $D_1$ and $D_2$. This approach reduces the number of stages needed in a bleach plant, reduces the amount of AOX produced, reduces the amount of chlorinated waste water for disposal and reduces the amount of bleaching chemicals needed. Eliminating at least one chlorine dioxide stage may increase fiber strength and pulp yield. Using the peracetate oxidant as a more selective oxidant for the E stage may increase fiber strength and pulp yield.

In some embodiments, the peracetate oxidant technology would typically be used after a pulping process (mechanical, chemical or enzymatic pulping) and may be used up stream or down stream of additional delignification stages such as oxygen delignification or enzymatic delignification. The potential benefit of using the peracetate oxidant chemistry before or after any of these earlier processing stages is to increase the surface area of the fibers, thereby improving access of the reactive oxygen species to the fiber interior for rapid delignification and brightening, higher throughput in the brightening stage, and reduced chemical use. For example, fiber brightening may be completed within 1-10 minutes of contact time with the peracetate oxidant formulation at an appropriate temperature and pH range. Another benefit of using the peracetate oxidant formulation for delignification and brightening is odor control during fiber processing and eliminating odors in fiber products.

In another embodiment, conducting fiber brightening with the peracetate oxidant formulation after a sulfide digester pulping stage will rapidly oxidize sulfide carryover and eliminate odors created by the digester process.

In another embodiment, conducting fiber treatment with the peracetate oxidant formulation after an oxygen delignification stage will remove lignin and non-lignin materials not removed by the oxygen delignification stage and eliminate odors created by the oxygen oxidation process.

In another embodiment, conducting fiber treatment with the peracetate oxidant formulation before an oxygen delignification stage will remove lignin and non-lignin materials not removed by the oxygen delignification stage and may enhance the performance and efficiency of an oxygen delignification stage.

In another embodiment, conducting fiber treatment with the peracetate oxidant formulation during an oxygen delignification stage will remove lignin and non-lignin materials not removed by the oxygen delignification stage and may enhance the performance and efficiency of an oxygen delignification stage.

Types of fiber treated in this invention include wood pulp and other fibers used in paper, packaging and molded fiber products including bamboo, *Eucalyptus*, wheat straw, rice, bagasse, palm, flax and other plant-based sources. The lignocellulosic pulp employed in the present invention can be prepared from any lignocellulose-containing material derived from natural sources such as, but not limited to, hardwood, softwood, gum, straw, bagasse and/or bamboo by various chemical, semichemical, thermal, mechanical or combination pulping processes. Chemical and semichemical pulping processes include, but not limited to kraft, modified kraft, kraft with addition of sulfur and/or anthraquinone, and sulfite. Mechanical pulping processes include, but not limited to stone groundwood, pressurized groundwood, refiner mechanical, thermo-refiner mechanical, pressure refined mechanical, thermo-mechanical, pressure/pressure thermo-mechanical, chemi-refiner-mechanical, chemi-thermo-mechanical, thermo-chemi-mechanical, thermo-mechanical-chemi, and long fiber chemi-mechanical pulp. Handbook for Pulp and Paper Technologist, ed. G. A. Smook (Atlanta, Ga., TAPPI Press, 1989) describes both chemical and mechanical pulping.

In some embodiments, the use of peracetate oxidant formulation is significantly safer than chlorine and chlorine dioxide. Peracetate oxidant solutions are composed of sodium peracetate salt, which is a water soluble solid in its native form. Salts in general have significantly lower vapor pressures than liquids and gases at room temperature. A small fraction of the sodium peracetate can be present as peracetic acid, however, peracetic acid is consumed by reactions with sodium peracetate and does not reach significant concentrations in solution. Exposure to sodium peracetate solution is limited to inhalation of an aerosol or mist and exposure to liquid concentrates.

For comparison, a 5% peracetic acid solution has a reported vapor pressure of 22 mm Hg (0.029 atm). Peracetic acid is a liquid in its native form with a boiling point of 25° C. The 8 hour time weighted average acute exposure guidelines (TWA-AEGL) in air are currently 0.52 mg/m$^3$ (level 1), 1.6 mg/m$^3$ (level 2) and 4.1 mg/m$^3$ (level 3).

Chlorine dioxide is a gas with a vapor pressure of greater than 1 atm and limited water solubility. Chlorine dioxide solubility limit in water is 0.8% wt/vol at 20° C., but rapidly off-gasses above 0.3%. The 8 h TWA permissible exposure limit (PEL) in air is currently 0.3 mg/m$^3$. The immediately dangerous to life or health (IDLH) concentration is 13.8 mg/m$^3$ and exposure to greater than 1187 mg/m$^3$ (430 ppm) can cause death within 30 minutes.

The use of elevated concentrations of chlorine dioxide in water treatment is particularly hazardous. For example, the head space of a tank containing water with 20 mg/L chlorine dioxide will slowly equilibrate to a head space concentration of 807 mg/m$^3$ at 25° C. and 1 atm according to Henry's law calculations. Pulp bleaching operations using chlorine dioxide at several hundred to several thousand mg/L concentrations and elevated temperatures pose severe exposure hazards over large areas if not properly contained. Gases are more difficult to contain than liquid solutions with low vapor pressures. Chlorine dioxide is also an explosive gas and can undergo explosive decomposition above 10% v/v chlorine dioxide in air. Above 14% explosions are violent. Explosive vapor concentrations can be achieved in pipes that are only partially filled with moderately concentrated chlorine dioxide solutions.

In some embodiments, a method provides for treating pulp in pulp and paper mills. The treating may consist of delignifying, bleaching and/or brightening the pulp. The methods may include providing a peracetate oxidant solution. The peracetate solution may include peracetate anions and a peracid. In some embodiments, the peracetate solution may include a pH from about pH 10 to about pH 12. In some embodiments, the peracetate solution has a molar ratio of peracetate anions to peracid ranging from about 60:1 to about 6000:1. In some embodiments, the peracetate solution has a molar ratio of peracetate to hydrogen peroxide of greater than about 16:1. The peracetate solution may provide delignifying, bleaching, and/or brightening pulp. In some embodiments, the peracetate oxidant solution kills the microbial population in the pulp. In some embodiments, the peracetate solution reduces the biofilms and corrosion.

In some embodiments, a method provides for microbial control by reducing the microbial load in contaminated water of water recycle loops. These water recycling loops include pulp and paper mills, feedstock slurry, water loops, feedstock processing systems and non-potable water systems. The methods may include providing a peracetate oxidant solution. The peracetate solution may include peracetate anions and a peracid. In some embodiments, the peracetate solution may include a pH from about pH 10 to about pH 12. In some embodiments, the peracetate solution has a molar ratio of peracetate anions to peracid ranging from about 60:1 to about 6000:1. In some embodiments, the peracetate solution has a molar ratio of peracetate to hydrogen peroxide of greater than about 16:1. The peracetate solution may provide bleaching, sanitizing and/or disinfection of contaminated water and surfaces. The peracetate oxidant solution may provide enhanced separation of microbes from contaminated water. In some embodiments, the peracetate oxidant solution kills the microbial population in the contaminated water. In some embodiments, the microbes are removed from the contaminated water. In some embodiments, the peracetate solution reduces the biofilms and microbial corrosion.

In some embodiments, a method provides for microbial control and reduction of oxidation byproducts in water treatment, bleaching and paper making using highly active peracetate oxidant solutions.

In some embodiments, the amount of peracetate oxidant solution used is dependent on the severity of contamination, the degree of microbial control desired and residual oxidant solution necessary for effective microbial control.

In some embodiments, the contaminated water can be sequentially dosed with peracetate oxidant solution until the degree of microbial control desired is reached and the sequential dosing has a synergistic effect on microbial control. The reducing of the microbial load prevents bacteria in the contaminated water from becoming anaerobic and prevents the formation of sulfides, ammonia, volatile organic acids which result in reduced release of volatile materials and odor control.

In some embodiments, a method is provided for the ability to combine the use of peracetate oxidant solution and an alternative oxidant for improved antimicrobial treatment of water. In some embodiments, the alternative oxidant is selected from the group consisting of chlorine, chlorine bleach, bromine, iodine and fluorine.

In some embodiments, a method is provided for reducing the microbial load in contaminated water previously treated with an alternative oxidant by treating with a peracetate oxidant solution for improved microbial control of water.

In some embodiments, heating or thermal activation of peracetate oxidant solutions to a temperature between about 38° C. to about 95° C. accelerates the formation of ROS daughter products as shown by greatly enhanced bleaching and biocidal activity with increasing temperature. Thermal activation that accelerates ROS production rate is useful for microbial control in heated environments and hot chemical sanitizing processes.

In some embodiments, a method is provided for reducing the microbial load in a slurry comprising containing a population of microbes with a peracetate oxidant solution; and mixing said slurry with the peracetate oxidant solution.

In some embodiments, the peracetate oxidant solutions are particularly suited for use in water with high salinity, alkalinity and contamination as they rely on reactive oxygen species whose performance is little impacted or enhanced by such conditions, in contrast to common Fenton and advanced oxidation processes that produce hydroxyl radical or ozonides as the primary ROS. The peracetate oxidant does not form bromate in bromide-containing water under typical treatment conditions, which is a benefit for treated water discharge. In some embodiments, the peracetate oxidant has a very low organic halide formation potential in wastewater treatment and pulp bleaching compared to chlorine and chlorine dioxide.

In some embodiments, the peracetate oxidant is generated at, or near, the point of use as an aqueous solution due to its high activity and relatively short half-life of minutes to hours depending on concentration and use conditions. The oxidant is active long enough to serve as an oxidant and/or biocide before it attenuates leaving benign and readily degradable residuals including oxygen, sodium acetate and glycerol.

BRIEF DESCRIPTION OF THE DRAWINGS

Advantages of the present invention may become apparent to those skilled in the art with the benefit of the following detailed description of the preferred embodiments and upon reference to the accompanying drawings.

Figure 1:
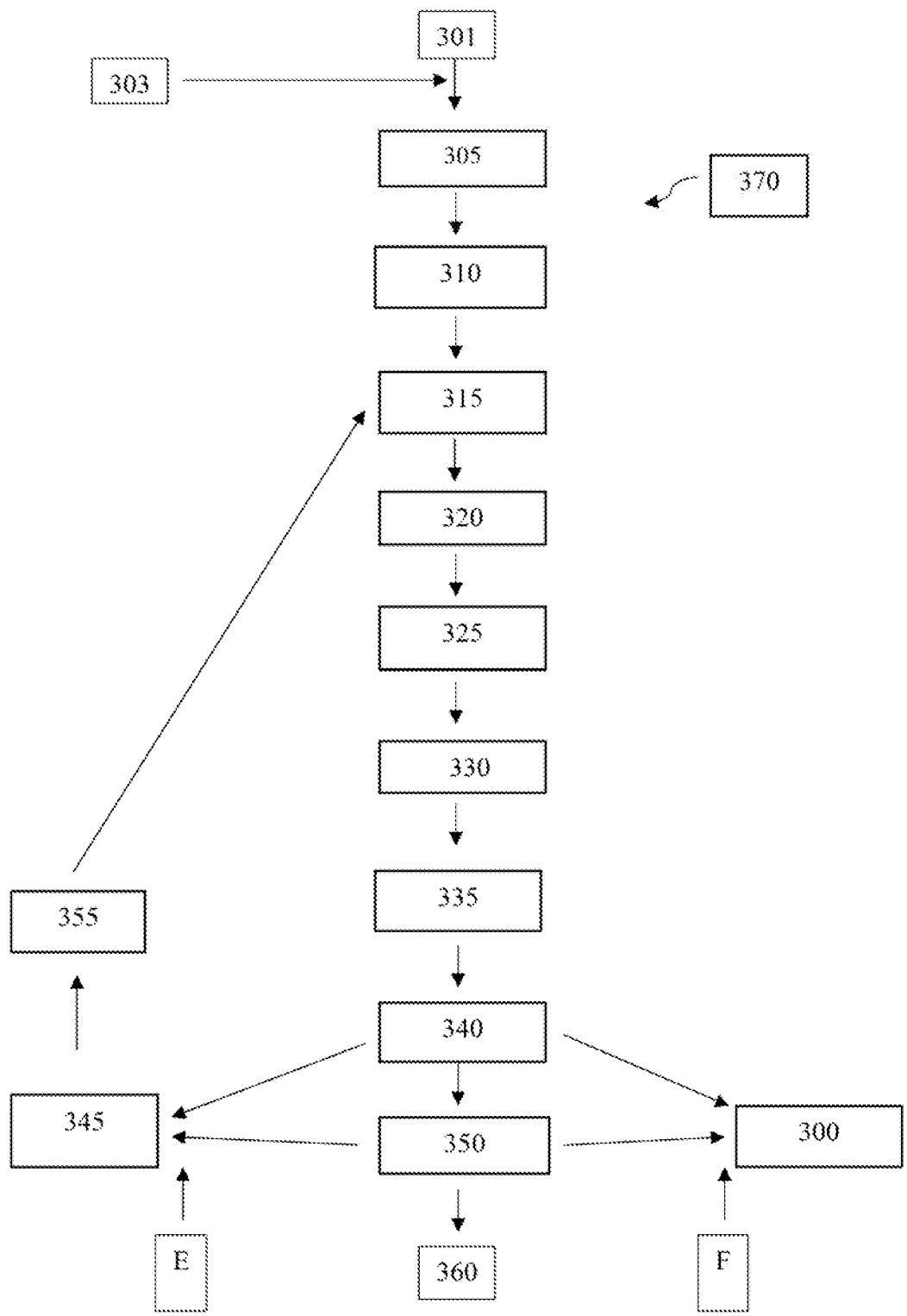
FIG. 1 is a simplified schematic diagram of an embodiment of a pulp and paper processing system.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the form disclosed, but on the contrary, the intention is to cover all modifications, equivalents and alternatives falling within the spirit and scope of the present invention as defined by the appended claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task. In some contexts, "configured to" may be a broad recitation of structure generally meaning "having a feature that" performs the task or tasks during operation. As such, the component can be configured to perform the task even when the component is not currently on.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112 paragraph (f), interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. Regarding the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for describing embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The term "contaminated water" as used herein generally refers to water containing undesirable chemical or biological species that are to be at least in part removed by oxidative treatment including bacteria, other microorganisms, salt, scaling minerals, transition metals, dissolved and suspended inorganic materials, dissolved and suspended organic materials, oils, non-oxidizing biocides, scale inhibitors, iron stabilizers, hydrogen sulfide, and naturally occurring radioactive materials (NORM).

The term "reactive oxygen species" as used herein generally refers to a species such as may include singlet oxygen ($^1O_2$), superoxide radical ($O_2^-$), hydroperoxyl radical (HOO·), hydroxyl radical (HO·, acyloxy radical (RC(O)—O·), and other activated or modified forms of ozone (e.g., ozonides and hydrogen trioxide). Each of these ROS has its own oxidation potential, reactivity/compatibility profile, compatibility/selectivity and half-life.

The term "reactive species oxidant" as used herein generally refers to oxidant formulations containing or capable of evolving at least one reactive oxygen species and can evolve at least one reactive carbon species. Such reactive species enhance the oxidative or reductive performance of the precursor formulation constituents.

The term "contaminated water source" as used herein generally refers to pipelines, tanks, and other equipment carrying raw waste water, greywater, ground water, tailing pond water, refinery waste water, oilfield produced water, various industrial and food processing waters, water recycling loops, pulp and paper mills, feedstock processing systems, cooling towers and water cooling loops, and non-potable water systems.

The term "microbes" as used herein generally refers to aerobic and anaerobic bacteria (slime formers, acid producers, metal depositors, nitrobacteria, sulfate reducers, nitrate reducers), fungi, algae, molds, and yeast.

The term "pulp" as used herein generally refers to a suspension of cellulose fibers in water consisting of any lignocellulose-containing material derived from natural sources such as, but not limited to, hardwood, softwood, bamboo, *Eucalyptus*, wheat straw, rice and other plant-based sources, straw, bagasse and/or bamboo and such pulp produced by various chemical, semichemical, thermalor, mechanical pulping processes or a combination pulping processes.

The terms "delignifying" and "delignification" as used herein generally refers to removal of lignin from wood and non-wood fibers by mechanical, chemical or enzymatic means or a combination thereof the polymer lignin from wood The term "bleaching" as used herein generally refers to a chemical process used to whiten and purify pulp and the processing of wood to decrease the color of the pulp and to make it whiter.

The term "brightening" as used herein generally refers to increasing the reflectance and/or whiteness of fibers, which may be related to a reduction in kappa number as a result of delignification and bleaching without the use of traditional bleaching to achieve a brightness of 65% ISO brightness units or greater.

The term "pulp treatment process" as used herein generally refers at least one of pulping, delignification and bleaching.

Embodiments

In some embodiments, the ROS-generating peracetate formulation of the present invention may be used for delignification and extraction of materials from pulp fibers for brightening and bleaching purposes. It may also be used for extracting lignin from cellulosic fibers for the recovery of lignin from the black liquor or spent oxidant liquor.

In some embodiments, the ROS generated by the parent peracetate formulation, particularly singlet oxygen, are the primary chemical species doing the delignification, brightening and bleaching of fibers. The direct reaction of peracetate with pulp is minimal, which contrasts with the use of peracetic acid in combination with hydrogen peroxide as the primary oxidants, which have much lower performance efficiency (and therefore, higher cost) for delignification, brightening and bleaching.

In some embodiments, the peracetate oxidant formulation of this invention produces singlet oxygen as the primary reactive oxidant species and therefore avoids damage of cellulose fibers relative to other chemical methods for delignification and bleaching. The peracetate oxidant formulation also performs well at its natural pH without the use of additional alkali, which also reduces to damage to cellulose fibers. Using the peracetate oxidant formulation to reduce or eliminate the amount of oxygen delignification and/or eliminate at least a portion of pulp bleaching with chlorine, chlorine dioxide or ozone can improve pulp yield, fiber strength, fiber quality and fiber product strength. The peracetate oxidant formulation provides the first known bulk source of singlet oxygen for pulp delignification and bleaching.

Singlet oxygen is well suited for oxidation of phenols, chlorinated phenols and similar electron-rich phenolic materials including lignin. Lignin generally consists of cross-linked polyphenolic materials created by enzyme-mediated polymerization of coniferyl, sinapyl and p-coumaryl alcohols. Singlet oxygen (which is not a radical) is relatively selective towards phenol oxidation and has little direct impact on cellulose fibers. In contrast, ozone and radicals including elemental chlorine, hydroxyl radical, hydroperoxyl radical, superoxide and even triplet oxygen are more reactive towards cellulose in conventional delignification and bleaching processes.

Studies of singlet oxygen oxidation of phenols has historically been conducted using photocatalytic methods to generate singlet oxygen in-situ. This method often involves irradiation of a solution containing a photosensitive dye (e.g., rose bengal, methylene blue) which transfers its photo-excited state energy to dissolved oxygen. Relying on a dye mediated photooxidation process is not practical for pulp delignification due to optically opaque pulp mixtures and the rapid breakdown of photosensitive dyes by singlet oxygen and other ROS.

In some embodiments, pH has a significant impact on the reactivity between singlet oxygen and lignin. Raising the pH close to or above the pKa of the phenolic compound (typically greater than pH 9 and preferably greater than pH 10) significantly accelerates oxidation. [Ref: Nowakowska, M.; Kepczynski, M.; Journal of Photochemistry and Photobiology A: Chemistry; 116 (1998) 251-256.] The oxidation of phenol by singlet oxygen in aqueous alkaline conditions was determined to proceed through a benzoquinone intermediate, which was further oxidized by singlet and triplet oxygen forming byproducts including carbon dioxide, maleic acid and fumaric acid. [Ref: Gerdes, R.; Wohrle, D.; Spiller, W.; Schneider, G.; Schnurpfeil, G.; Schulz-Ekloff, G.; Journal of Photochemistry and Photobiology A: Chemistry; 111 (1997) 65-74.]

Polychlorinated phenols are one of the major absorbable organic halogens (AOX) that may be discharged in pulp bleaching effluents. Also in the AOX category are dioxins, furans and other halogenated organic materials. AOX formation is highly dependent on the lignin content (proportional to kappa number) of the pulp prior to bleaching. The more reduction in kappa number prior to bleaching the less AOX formation potential. In some embodiments, the ROS-generating peracetate oxidant formulation can reduce kappa number (lignin content) significantly.

For example, the peracetate oxidant formulation can reduce hardwood kappa numbers of 14-20 down to 5-12 in a single stage and can reduce softwood kappa numbers of 30-35 down to 15-25 in a single stage. North American softwood (pine) pulp fiber (kappa no. 35.42) and hard wood pulp fiber (kappa no. 16.00) were treated with the peracetate oxidant formulation at 5% pulp consistency and 65° C. and the natural pH of the pulp. The pulp slurries, or mixtures, were prepared and a 2.0% wt/vol peracetate solution was added in the appropriate amount to make the initial concentrations of 0.20% and 0.40%. The samples were contained ion 1 L glass beakers heated in a water bath. Delignification was conducted for 5 minutes and 30 minutes to compare the extent of Kappa number reduction. Mixing was conducted over time. At the end of the reaction time period the oxidant residual was quenched by washing the pulp samples with 1.5 L of tap water through a screen lined with cheese cloth. Kappa number measurements were conducted on pulp samples stored damp after determining the percent solids of each sample. Kappa numbers were measured in duplicate or triplicate and a summary of test results is provided in Table 7.

The pH of pulp mixtures was measured with a high sodium pH electrode put directly into the pulp slurry. A thermocouple for temperature compensation of the pH reading was placed in the pulp during measurement.

Addition of the peracetate oxidant had little to no impact on the initial pH of the pulp mixture at its natural pH. The pH of the pulp mixtures decreased over time and the magnitude of pH reduction increased with increasing kappa reduction, reaction time and initial oxidant concentration. Other tests conducted with the initial pH of pulp mixtures adjusted with sodium hydroxide to pH 11.0-11.5 produced less kappa number reduction for a given set of conditions and higher final pH.

Conducting delignification tests at greater than about pH 10.5 did not improve delignification performance. At pH 11 and greater delignification of wood pulp was partially inhibited (kappa number reduction was less). Previous results reported by Gerdes et al. showed that high pH enhances further breakdown of phenols resulting in increased oxygen consumption. Conducting delignification at less than pH 11 is more efficient for lignin extraction with the peracetate oxidant formulation, which may be a result of oxidative reactivity of phenols being moderated to slow further oxygen reactions with the lignin.

A direct observation of ongoing oxidation reactions with extracted lignin was slow bleaching of the color from spent peracetate oxidant liquors containing several hundred ppm of active oxidant residual. Over several hours the color was bleached to very pale hues. (i.e., yellow to orange-colored quinone-like oxidation byproducts being further oxidized to nearly colorless byproducts). Reactions of the peracetate oxidant with extracted lignin may compete or interfere with delignification of fiber as kappa number increases.

In some embodiments, delignification performance of the ROS-generating peracetate oxidant formulation is high, even at pH 9 or less. Applying the peracetate oxidant in high doses in a single step process is effective, but this approach can be costlier. The capital cost for the peracetate oxidant technology is almost negligible compared to traditional processes including oxygen delignification and chlorine dioxide bleaching lines. Minimal capital cost may offset the total cost of ownership to use the peracetate oxidant technology in facilities having little to no existing infrastructure for brightening or bleaching fiber.

In some embodiments, methods to use the ROS-generating peracetate oxidant formulation more efficiently were developed to reduce operating costs of feedstocks so that it can directly compete with chlorine dioxide on a cost basis when considering reducing chlorine chemicals, reducing chlorine bleaching steps, reducing AOX formation and emissions, reducing bleaching effluent for treatment, and reducing capital costs relative conventional mill infrastructure. Additional financial benefits may be realized in lower corrosion-caused maintenance costs, higher pulp yields, greater fiber product strength and increased throughput of an existing pulp line.

In some embodiments, the ability to conduct delignification at medium pulp consistency (10-20% oven dried fiber by weight) has a significant impact on economics compared to low consistency processing. At medium consistency, the mixing efficiency and rate of pulp fibers with the peracetate oxidant solution is a critical parameter for maximizing the rate and extent of delignification.

For example, a low concentration of peracetate oxidant was used to examine the impact of different mixing methods over a ten minute period at 70° C. A summary of test results is provided in Table 8 (softwood pulp) and Table 9 (hardwood pulp).

Vigorous mixing of the softwood pulp for 10 minutes with 1800 ppm initial oxidant dose produced a 36.7% kappa reduction. Limiting the mixing to just the first minute decreased the kappa reduction to 31.0%. Conducting the test with a first oxidant dose of 900 ppm and mixing for 5 minutes then adding another 900 ppm oxidant dose and mixing for another 5 minutes produced a 27.1% kappa reduction.

Repeating the above two-step addition of oxidant for the softwood with 800 and 1600 ppm doses produced a 24.6% kappa reduction. The 1600 ppm dose was added at 5 minutes on top of a 285 ppm measured residual for a combined maximum concentration of 1885 ppm. For the softwood pulp the kappa reduction was greatest with the highest initial concentration of oxidant with only a single reaction step. The higher oxidant demand corresponding with the higher initial kappa number may be caused by greater lignin concentration and/or reactivity of extractible materials in the softwood black liquor. The observed oxidant demand of extracted materials appears to reduce the concentration of singlet oxygen available to react with the pulp, especially when a partial extraction is done prior to the second oxidant dose in the softwood two-step experiments (the final oxidant concentration was 760 mg/L). The same tests were repeated conducted on the hardwood pulp and the results shown in Table 9.

Vigorous mixing of the hardwood pulp for 10 minutes with 1800 ppm initial oxidant dose produced a 28.9% kappa reduction. Reducing the mixing to just the first minute decreased the kappa reduction to 20.6%. Conducting the test with a first oxidant dose of 900 ppm and mixing for 5 minutes then adding another 900 ppm oxidant dose and mixing for another 5 minutes produced a 31.9% kappa reduction.

Repeating the above two-step addition of oxidant for the hardwood with 800 and 1600 ppm doses produced a 38.9% kappa reduction. The 1600 ppm dose was added at 5 minutes on top of a 285 ppm measured residual for a combined maximum concentration of 1885 ppm. For the hardwood pulp the kappa reduction was greatest for the two-step process with the highest second dose concentration. The lower overall oxidant demand corresponding with the lower initial kappa number may not be significantly limiting the concentration of singlet oxygen available to react with the pulp in the hardwood two-step experiments (the final oxidant concentration was 1000 mg/L).

Delignification of pulps with low to medium kappa (i.e., initial kappa numbers of 12-20) benefits significantly from two-step oxidation processes. Delignification of pulps with medium kappa (i.e., initial kappa numbers of 20-40) is expected to benefit from a two-step delignification process, but removal of the black liquor (oxidant liquor) after the first step may be required. This oxidant liquor may still contain active oxidant and can be used in an initial wash step of brownstock.

In some embodiments, methods of using the ROS-generating peracetate oxidant formulation are influenced by the ROS generation behavior of the peracetate oxidant formulation. Thermal acceleration of the reaction(s) that produce ROS, especially singlet oxygen, from the "parent" peracetate formulation is particularly important to performance. Several process variables are important for pulp delignification, brightening and bleaching and these variables are incorporated into preferred methods for efficient use of the peracetate oxidant formulation. In some embodiments, a method treating pulp further comprises a method of heating or maintaining the heat of the pulp in a range from about 38° C. to about 95° C., more preferably 65° C. to about 75° C. prior to or following contacting with a peracid composition. Thermal activation that accelerates ROS production rate is useful for treating the pulp. Peracetate oxidant solution can be thermally activated to enhance its production of ROS and biocidal activity. Thermal activation is useful throughout the treatment process. For example, pulp bleaching is very slow at room temperature (takes more than 1 hour to achieve modest bleaching) but is very rapid at 70° C.

In some embodiments, a method of reducing the microbial load in a slurry may include: providing a slurry containing a population of microbes and providing a peracid composition. The peracid composition may include a mixture of an alkali concentrate, a hydrogen peroxide and an acyl donor having a pH value ranging from about pH 10 to about pH 12. The peracid composition may include a first molar ratio of peracid anion to peracid acid ranging from about 60:1 to 6000:1. The peracid composition may include a second molar ratio of peracetate to hydrogen peroxide of 16:1 or more. The method may include contacting the peracid composition with the slurry. In some embodiments, the method may include mixing, after the contacting of the peracid composition and the slurry.

In some embodiments, a slurry for reducing the microbial load is selected from slurries of wood pulp and wood products, silica, polymers, polysaccharide gels, biomass feedstocks for fermentation, recycled paper and textiles and materials processed as slurries.

In an embodiment, the rate of ROS generation by the peracetate formulation is directly proportional to the rate of peracetate concentration decline. In some embodiments, the rate of ROS generation is thermally activated to accelerate delignification. Measurement of peracetate concentration over time was conducted in clean tap water and in 5% consistency hardwood pulp at 70° C., which is a common temperature for pulp delignification and bleaching processes in a paper mill.

Figure 3:
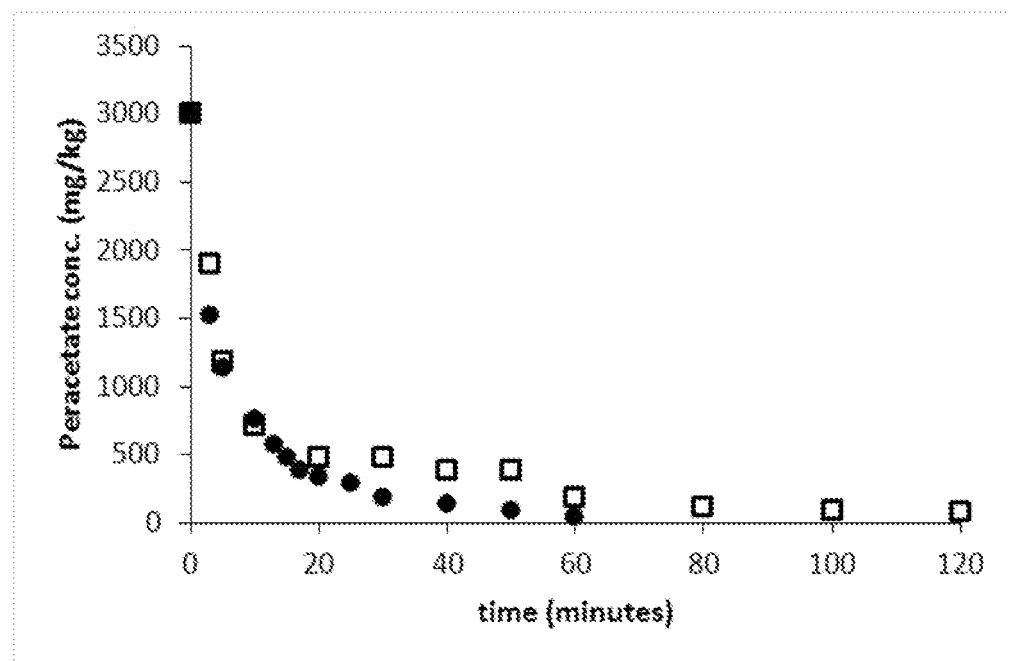
FIG. 3 is a graphical representation of an embodiment of peracetate concentration over time at 70° C.

In a first test a 250 mL solution of tap water containing an initial peracetate concentration of 3000 mg/L at 70° C. was made by mixing 37.5 mL of a 2.0% wt/vol solution of the peracetate formulation concentrate (made at room temperature) into 212.5 mL of tap water already heated to 70° C. in a 1 L glass beaker in a hot water bath. Samples were removed for analysis at regular time intervals and the results presented in FIG. 3, open squares represent the tap water samples. The initial pH was 9.0 and the final pH was 5.8. The initial ORP was 540 mV vs SHE, which increased to a maximum of 785 mV in 30 minutes.

In a second test a 250 mL slurry of a north American hard wood pulp fiber (16.0 kappa number) at 5% consistency and 70° C. containing an initial peracetate concentration of 3000 mg/L was made by mixing 37.5 mL of a 2.0% wt/vol solution of the peracetate formulation concentrate (made at room temperature) into 200 mL of tap water with 12.5 g (oven dry weight) of pulp fiber already heated to 70° C. in a 1 L glass beaker in a hot water bath. The slurry was thoroughly mixed and samples of the oxidant liquor were removed and filtered for analysis at regular time intervals. The results are presented in FIG. 3 solid circles represent the pulp slurry samples. The initial pH was 8.8 and the final pH was 6.4. The initial ORP was 675 mV vs SHE, which increased to a maximum of 850 mV in 25 minutes.

The peracetate concentration decreased at a similar rate for both tests over the first 10-20 minutes. After about 20 minutes the residual peracetate concentration in tap water persisted longer at a higher concentration than the residual in the pulp slurry. At 30 minutes the peracetate residual in tap water was about 9.6% higher than the residual in the pulp slurry relative to the initial peracetate concentration.

The reaction between peracetate ion and its conjugate acid form to produces singlet oxygen ($^1O_2$) follows second order kinetics. An initial pre-equilibrium of peracetate and peracetic acid is fast while the bimolecular reaction is rate limiting, as depicted in the chemical reaction scheme in FIG. 4. Acid protons may be available in a solution from a variety of materials with pKa less than peracetate including acids, acid groups on a material, contaminants and oxidation byproducts. The second-order reaction rate kinetics for the primary singlet oxygen reaction dominate the observed initial rate behavior. There are also a variety of other reactions that may occur at elevated temperature (small delta) and/or in the presence of reactive materials or impurities which are known to catalyze the disproportionation of peracetate and/or peracetic acid to ROS and acetyl radicals. A one electron ($e^-$) reduction of singlet oxygen can produce superoxide, which is in equilibrium with hydroperoxyl radical in the presence of acidity. For pulp delignification, the formation of superoxide is preferred so as to limit damage to cellulose fibers by free radicals.

Figure 5:
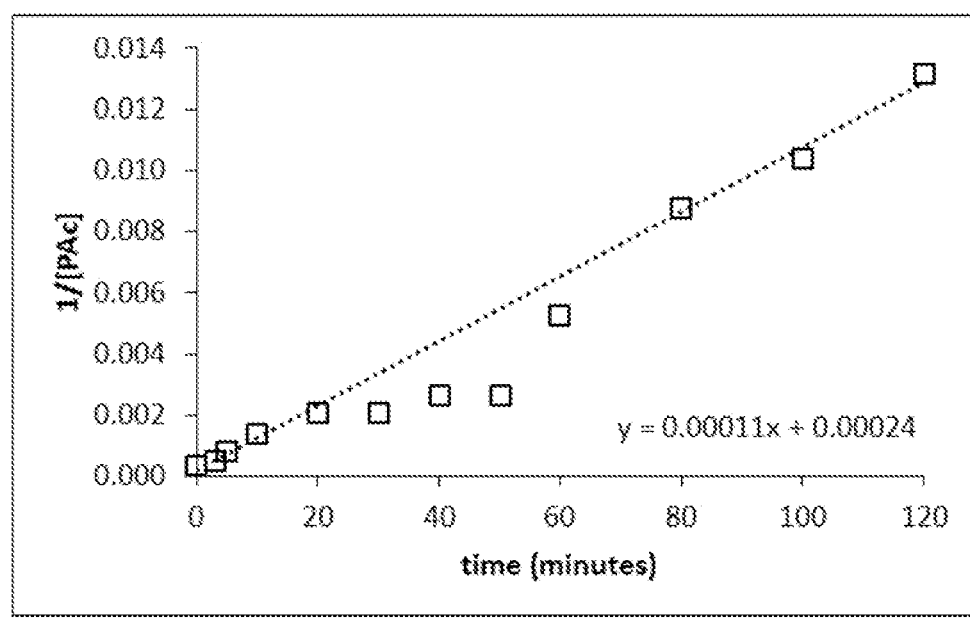
FIG. 5 is a simplified graphical representation of an embodiment of second order kinetics of peracetate concentration in water at 70° C.

Under the initial pH conditions in tap water, the peracetate anion (initially produced as the sodium peracetate salt) is in large excess of the acid form, but acidity in the water (e.g., bicarbonate, oxidant hydrolysis products) will convert a portion of the peracetate to the protonated, acid form. Plotting 1/[peracetate] in FIG. 5 shows an initial linear region up to about 20 minutes, which is consistent with second order reaction behavior dominating the kinetics of peracetate concentration decline. The slope of the linear fit is proportional to the reaction rate constant. After 20 minutes the rate of peracetate decline slows and departs from second order behavior, but then resumes with second order behavior by 80 minutes at the same slope (rate constant) as initially measured.

The temporary departure from second order behavior suggests the buildup of ROS species or complexes that may interfere with the singlet oxygen forming reaction occurred until they dissipated or were consumed over nearly an hour. The buildup of ROS species can only occur if they persist in solution longer than just singlet oxygen, which has a lifetime of only several microseconds in water.

Figure 4:
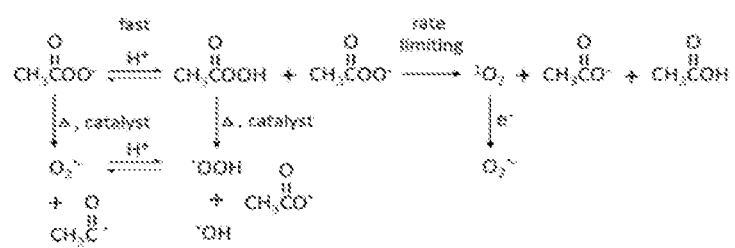
FIG. 4 is a simplified schematic of singlet oxygen production and several other reactions which produce ROS.

A longer-lived, high ORP combination of singlet oxygen, superoxide and other radical fragments caused by thermal or catalytic disproportionation of the parent oxidant has been described in FIG. 4 here. A one electron reduction of singlet oxygen can form superoxide in-situ. A buildup of these species in clean water during the initial rapid generation of ROS, where they are not consumed by reactive substrates or impurities, may disrupt the second-order bimolecular reaction. Once these longer lived ROS species are dissipated or consumed the second-order reaction can dominate the observed peracetate decline rates again.

Figure 6:
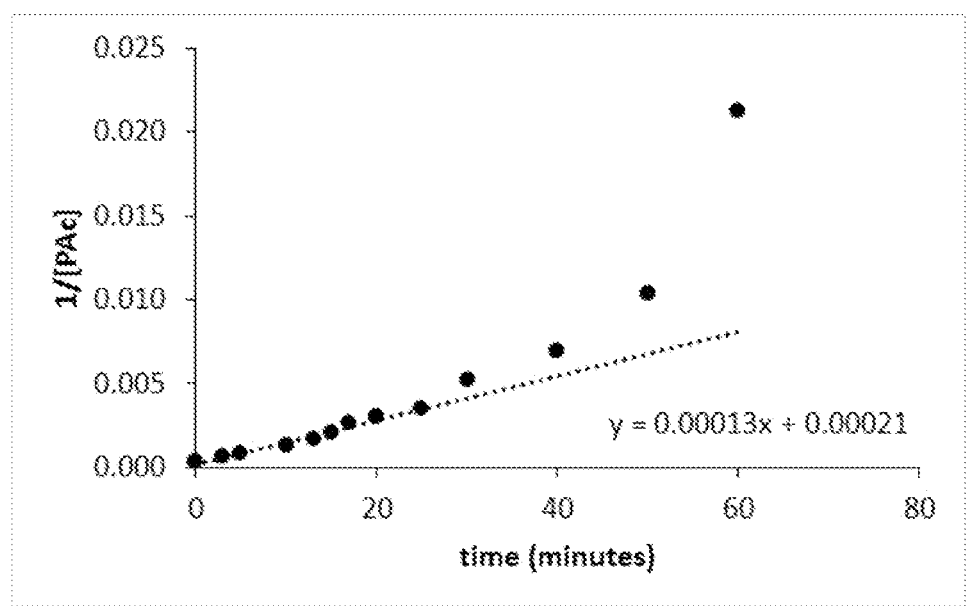
FIG. 6 is a simplified graphical representation of an embodiment of second order kinetics of peracetate concentration in 5% pulp fiber at 70° C.
Figure 7:
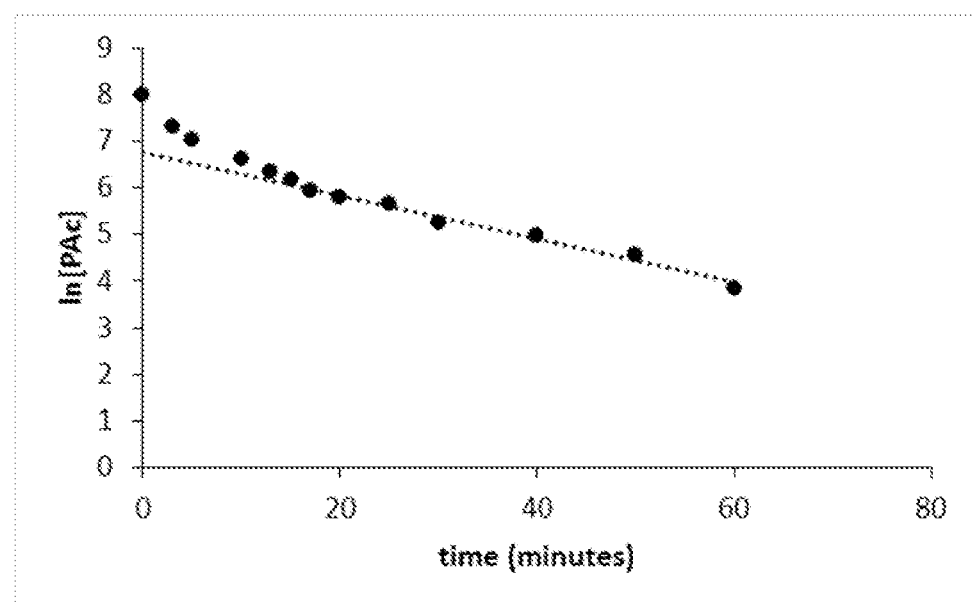
FIG. 7 is a simplified graphical representation of an embodiment of pseudo-first order kinetics of peracetate concentration in 5% pulp fiber at 70° C.

The initial and final pH in the wood pulp mixture are similar to those in tap water. Plotting 1/[peracetate] in FIG. 6 shows an initial linear region up to about 20 minutes, which is consistent with second order reaction behavior dominating the initial kinetics of peracetate concentration decline. The linear slope (rate constant) in the 1/[peracetate] plots over the first 20-25 minutes is about 15% greater for pulp over clean tap water indicating that additional reactions of peracetate in the pulp environment are increasing the observed rate. After the first 20-25 minutes in the pulp sample the rate of peracetate decline follows a pseudo-first order behavior as shown by a linear relationship in the ln[peracetate] plot in FIG. 7. This behavior is dramatically different than that observed in clean tap water. In the pulp environment, the ROS will be consumed by reactions with lignin, hemicellulose, black liquor and other reactive materials or impurities present, thus not allowing ROS to build up significantly in the mixture. As the peracetate concentration decreases and the singlet oxygen reaction slows the rates of other peracetate-consuming reactions may compete making the peracetate decline appear to transition to a pseudo-first-order reaction behavior.

This behavior indicates that nearly all of the peracetate is being consumed by reactions that evolve ROS or other reactions native to the peracetate. There is an unexpectedly small amount of peracetate (approximately 10% by concentration, 15% by rate constant) that may be consumed in the hardwood pulp by direct reactions with materials including black liquor carry-over, reactions catalyzed by metal impurities (e.g., Fe, Mn), and readily oxidized hydrocarbons.

The ROS, which are dominated by singlet oxygen generated by the peracetate formulation, are doing the majority of the delignification, brightening and bleaching reactions in pulp. Furthermore, the best ROS generation rate and concentration is within the first 10-15 minutes of applying the peracetate solution for pulp delignification under these test conditions and initial peracetate oxidant concentration.

Fiber products, including fiber board and molded fiber products, produced from pulps of various types used in food packaging and compostables are generally unbleached if chlorine and chlorine dioxide are excluded from the processing. Producing these products with brightened (e.g., 65 ISO brightness units or greater) or near-white grades of fiber without the use of traditional bleaching lines is desirable. In some embodiments, using the peracetate oxidant technology can readily provide a rapid brightening stage over a wide range of production capacity and can be implemented rapidly with minimal capital outlay and space requirements. For existing pulp and paper mills the peracetate oxidant technology is a relatively simple, safe and low-cost retrofit or drop-in replacement. The byproducts of the peracetate oxidant formulation do not contain chlorides and are compatible for being sent to the recovery boiler in a closed-cycle mill process.

In an embodiment, a method of using the peracetate oxidant formulation in bleaching sequences. For example, a conventional four-stage bleaching sequence may use the pulp treatment stages of chlorine dioxide ($D_0$), oxidative extraction with alkaline hydrogen peroxide ($E_{OP}$), chlorine dioxide ($D_1$), and chlorine dioxide ($D_2$). This bleaching sequence may be abbreviated as D(EOP)DD. Hydrogen peroxide is used in the sequence to reduce chlorine dioxide use.

In some embodiments, the peracetate oxidant solution may be used prior to the bleaching sequence (allowing its spent liquor to be sent to the recovery boiler) such that at least one of the chlorine dioxide stages, such as $D_2$, may be eliminated. This approach reduces the number of stages needed in a bleach plant, reduces the amount of AOX produced, reduces the amount of chlorinated waste water for disposal and reduces the amount of bleaching chemicals needed. Eliminating one chlorine dioxide stage may increase fiber strength and pulp yield.

In some embodiments, the peracetate oxidant solution may be used within the bleaching sequence as a replacement for the $E_{OP}$ stage. The peracetate oxidant is more effective than hydrogen peroxide for removing or extracting residual lignin and is more selective oxidant than alkaline hydrogen peroxide. The greater performance of the peracetate solution may eliminate at least one chlorine dioxide stage, such as eliminating $D_2$ or eliminating $D_1$ and $D_2$. This approach reduces the number of stages needed in a bleach plant, reduces the amount of AOX produced, reduces the amount of chlorinated waste water for disposal and reduces the amount of bleaching chemicals needed. Eliminating at least one chlorine dioxide stage may increase fiber strength and pulp yield. Using the peracetate oxidant as a more selective oxidant for the $E_{OP}$ stage may increase fiber strength and pulp yield.

In an embodiment, the peracetate oxidant technology would typically be used after a pulping process (mechanical, chemical or enzymatic pulping) and may be used down stream of additional delignification stages such as oxygen delignification or enzymatic delignification. The potential benefit of using the peracetate oxidant chemistry after any of these earlier processing stages is to increase the surface area of the fibers, thereby improving access of the reactive oxygen species to the fiber interior for rapid delignification and brightening, higher throughput in the brightening stage, and reduced chemical use. For example, fiber brightening may be completed within 5-10 minutes of contact time with the peracetate oxidant formulation at an appropriate temperature and pH range. Another benefit of using the peracetate oxidant formulation for delignification and brightening is odor control during fiber processing and eliminating odors in fiber products.

In some embodiments, conducting fiber brightening with the peracetate oxidant formulation after a sulfide digester pulping stage will rapidly oxidize sulfide carryover and eliminate odors created by the digester process.

In another embodiment, conducting fiber treatment with the peracetate oxidant formulation after an oxygen delignification stage will remove lignin and non-lignin materials not removed by the oxygen delignification stage and eliminate odors created by the oxygen oxidation process.

In another embodiment, conducting fiber treatment with the peracetate oxidant formulation before an oxygen delignification stage will remove lignin and non-lignin materials not removed by the oxygen delignification stage and may enhance the performance and efficiency of an oxygen delignification stage.

In another embodiment, conducting fiber treatment with the peracetate oxidant formulation during an oxygen delignification stage will remove lignin and non-lignin materials not removed by the oxygen delignification stage and may enhance the performance and efficiency of an oxygen delignification stage. Use of peracetate oxidant during the delignification stage involves elevated pressures (6-8 bar), elevated temperatures (80° C. to about 120° C.) and retention times of 30-60 minutes.

Types of fiber treated in this invention include wood pulp and other fibers used in paper, packaging and molded fiber products including bamboo, *Eucalyptus*, wheat straw, rice, bagasse, palm, flax and other plant-based sources. The lignocellulosic pulp employed in the present invention can be prepared from any lignocellulose-containing material derived from natural sources such as, but not limited to, hardwood, softwood, straw, bagasse and/or bamboo by various chemical, semichemical, mechanical or combination pulping processes. Chemical and semichemical pulping processes include, but not limited to kraft, modified kraft, kraft with addition of sulfur and/or anthraquinone, and sulfite. Mechanical pulping processes include, but not limited to stone groundwood, pressurized groundwood, refiner mechanical, thermo-refiner mechanical, pressure refined mechanical, thermo-mechanical, pressure/pressure thermomechanical, chemi-refiner-mechanical, chemi-thermo-mechanical, thermo-chemi-mechanical, thermo-mechanical-chemi, and long fiber chemi-mechanical pulp. Handbook for Pulp and Paper Technologist, ed. G. A. Smook (Atlanta, Ga., TAPPI Press, 1989) describes both chemical and mechanical pulping.

In some embodiments, using peracetate oxidant formulation is significantly safer than chlorine and chlorine dioxide. Peracetate oxidant solutions are composed of sodium peracetate salt, which is a water soluble solid in its native form. Salts in general have significantly lower vapor pressures than liquids and gases at room temperature. A small fraction of the sodium peracetate can be present as peracetic acid, however, peracetic acid is consumed by reactions with sodium peracetate and does not reach significant concentrations in solution. Exposure to sodium peracetate solution is limited to inhalation of an aerosol or mist and exposure to liquid concentrates.

For comparison, a 5% peracetic acid solution has a reported vapor pressure of 22 mm Hg (0.029 atm). Peracetic acid is a liquid in its native form with a boiling point of 25° C. The 8 hour time weighted average acute exposure guidelines (TWA-AEGL) in air are currently 0.52 mg/m$^3$ (level 1), 1.6 mg/m$^3$ (level 2) and 4.1 mg/m$^3$ (level 3).

Chlorine dioxide is a gas with a vapor pressure of greater than 1 atm and limited water solubility. Chlorine dioxide solubility limit in water is 0.8% wt/vol at 20° C., but rapidly off-gasses above 0.3%. The 8 h TWA permissible exposure limit (PEL) in air is currently 0.3 mg/m$^3$. The immediately dangerous to life or health (IDLH) concentration is 13.8 mg/m$^3$ and exposure to greater than 1187 mg/m$^3$ (430 ppm) can cause death within 30 minutes.

The use of elevated concentrations of chlorine dioxide in water treatment is particularly hazardous. For example, the head space of a tank containing water with 20 mg/L chlorine dioxide will slowly equilibrate to a head space concentration of 807 mg/m$^3$ at 25° C. and 1 atm according to Henry's law calculations. Pulp bleaching operations using chlorine dioxide at several hundred to several thousand mg/L concentrations and elevated temperatures pose severe exposure hazards over large areas if not properly contained. Gases are more difficult to contain than liquid solutions with low vapor pressures. Chlorine dioxide is also an explosive gas and can undergo explosive decomposition above 10% v/v chlorine dioxide in air. Above 14% explosions are violent. Explosive vapor concentrations can be achieved in pipes that are only partially filled with moderately concentrated chlorine dioxide solutions.

Figure 8:
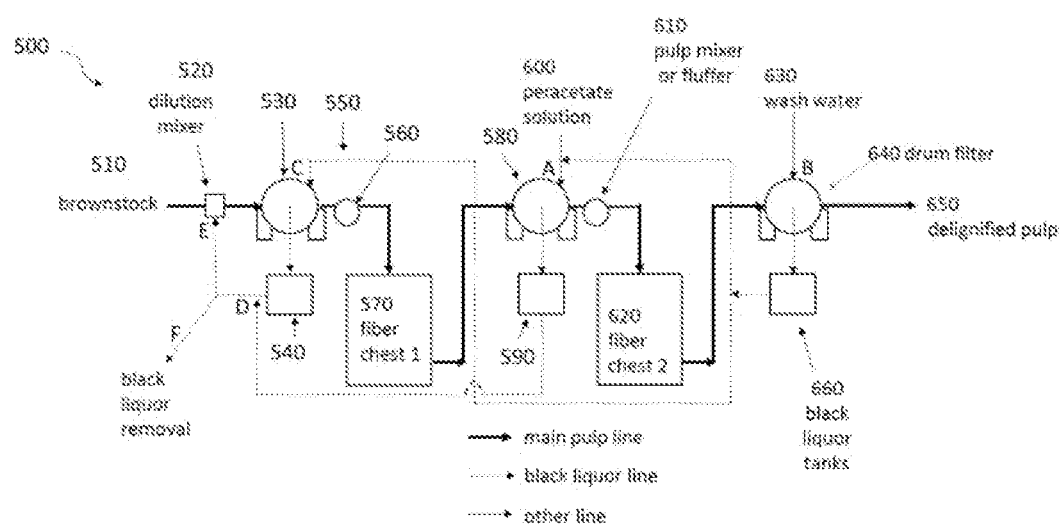
FIG. 8 a simplified schematic of a counter-flow delignification process.

Referring now to an exemplary counter-flow delignification process as shown in FIG. 8 for illustrative purposes only, designed to reduce consumption of the peracetate oxidant formulation. In general, an oxidant dose is added to a pulp stream at a primary addition point where the pulp and oxidant are contacted together and mixed. After a period of time the oxidant liquor containing residual active oxidant is separated from the pulp and conveyed to a secondary addition point, upstream of the primary addition point where untreated pulp and oxidant liquor are contacted together and mixed. The initial oxidant demand of the untreated pulp is reduced by the time it reaches the primary oxidant addition point.

An example of a counter-flow delignification process 500 is illustrated in FIG. 8. A source pulp or brownstock 510 is fed into the process in the forward-flow direction. The brownstock 510 may be coming from an upstream chemical digester, enzymatic process, oxygen delignification stage or from a market pulp supply. The brownstock is heated to or maintained at a temperature of 65-75° C. entering the process. The brownstock passes through a dilution mixer 520 and is then dewatered in a first wash stage (a drum filter 530 in this example) to about 15% consistency. The separated black liquor is collected in a first black liquor tank 540.

Prior to exiting the first filter stage 530 the pulp is showered with a black liquor stream 550 containing a residual amount of oxidant, then passes through a pulp mixer or pulp fluffer 560 and into a first fiber chest 570. The residence time in the fiber chest may be several minutes. The fiber is pumped from the first fiber chest 570 into the second wash stage 580 where it is dewatered to up to about a 15% consistency. The separated black liquor is collected in a second black liquor tank 590.

Prior to exiting the second filter stage 580 the pulp is showered with a peracetate oxidant stream 600 containing a residual amount of oxidant, then passes through a pulp mixer or pulp fluffer 610 and into a second fiber chest 620. The residence time in the fiber chest may be several minutes. The fiber is pumped from the second fiber chest 620 into the third wash stage 640 where it is showered and washed with clean water 630 and dewatered to up to about a 15% consistency. The separated black liquor wash is collected in a third black liquor tank 660. The delignified pulp 650 is then conveyed to the next storage or processing stages in the particular mill or facility.

In some embodiments, oxidation chemistry may be used for treatment of pulp as well as microbial control of contaminated water, reducing biological growth, disinfecting and sanitizing. The oxidation chemistry used may have minimal impacts on pH and scaling potential of fluids. A relatively short-lived active oxidant may be a benefit for avoiding negative impacts on pulp quality, paper quality, fermentation feedstock quality, food product quality and for minimizing oxidant corrosivity and environmental impacts. Selectivity of the oxidation chemistry towards different materials is also desirable for efficiency of oxidant use, compatibility with a variety of materials and avoidance of unnecessary or undesirable side reactions. Oxidant solutions that generate a variety of reactive oxygen species (ROS) in their treatment environments may be good candidates for achieving some or all of these attributes.

ROS may be generated in-situ by several chemical methods including the Fenton catalytic cycle with hydrogen peroxide and iron catalysts (produces hydroxyl and superoxide radicals), combining ozone with hydrogen peroxide (produces ozonides and oxygen-based radicals), and combining hypochlorite with hydrogen peroxide (produces singlet oxygen). Other methods of generating ROS may include photochemical approaches, which are generally very dilute in ROS and are not practical for large volume treatment systems or for highly scaling fluids or fluids with high turbidity.

Some ROS (e.g., hydroxyl radical and ozonides) are too short lived and too reactive to be practical in highly contaminated or hydrocarbon environments. Salt and carbonate may rapidly quench the hydroxyl radical. Ozone and stronger oxidants, like hydroxyl radical, oxidize salts to form toxic chlorate and bromate byproducts. Chlorine-containing oxidant formulations are typically more corrosive than peroxides, are less efficient for $H_2S$ oxidation and rapidly chlorinate unsaturated hydrocarbons.

In some embodiments, a method provides for treating pulp and microbial control in water recycling loops, pulp and paper mills, cooling towers and water loops, feedstock processing systems, and non-potable water systems. The methods may include providing a preferred ROS-producing oxidant formulation, peracetate oxidant solution.

In some embodiments, one preferred ROS-producing oxidant formulation is a peracetate solution. The peracetate solution may include generating an alkaline hydrogen peroxide solution from the combination of an alkali and a hydrogen peroxide concentrate, mixing the alkaline hydrogen peroxide solution with an acyl donor such that a peracetate solution concentrate is formed. In some embodiments, the peracetate solution may include peracetate anions and a peracid. In some embodiments, the peracetate solution may include a pH from about pH 10 to about pH 12. In some embodiments, the peracetate solution has a molar ratio of peracetate anions to peracid ranging from about 60:1 to about 6000:1. ROS-generating peracetate oxidant solutions may contain no hydrogen peroxide, and are produced on site and on demand at alkaline pH. The peracetate oxidant solution produces multiple ROS by itself and when placed into contaminated environments. In some embodiments, the ROS most important in peracetate oxidant solutions include singlet oxygen, superoxide radical, hydroperoxyl radical, acetyloxy radical and potentially other radical fragments. When a combination of these ROS are generated together in peracetate oxidant solutions they produce an oxidative-reductive potential (ORP) response in water that may exceed 900 mV (vs standard hydrogen electrode) around pH 7. These solutions may be more convenient and effective to use than other approaches. The dominant ROS may be selectively reactive such that they are effective in a variety of environments.

In some embodiments, a method may include making a reactive species formulation. The method may include providing an alkaline hydrogen peroxide solution. The method may include contacting the alkaline hydrogen peroxide solution with an acyl donor. A peracid concentrate may be produced by the contacting of the alkaline hydrogen peroxide with the acyl donor. The peracid concentrate may have a molar ratio of hydrogen peroxide to acyl donor reactive groups ranging from about 1:1.25 to about 1:4. The method may include maintaining the peracid concentrate pH value in a range from about pH 10 to about pH 12.

In some embodiments, a method of reducing the microbial load in a slurry may include: providing a slurry containing a population of microbes and providing a peracid composition. The peracid composition may include a mixture of an alkali concentrate, a hydrogen peroxide and an acyl donor having a pH value ranging from about pH 10 to about pH 12. The peracid composition may include a first molar ratio of peracid anion to peracid acid ranging from about 60:1 to 6000:1. The peracid composition may include a second molar ratio of peracetate to hydrogen peroxide of 16:1 or more. The method may include contacting the peracid composition with the slurry. In some embodiments, the method may include mixing, after the contacting of the peracid composition and the slurry.

In some embodiments, a slurry for reducing the microbial load is selected from slurries of wood pulp and wood products, silica, polymers, polysaccharide gels, biomass feedstocks for fermentation, recycled paper and textiles and materials processed as slurries.

In some embodiments, the peracetate oxidant solution is shown to reduce toxic organic halide formation (e.g., chlorinated phenols, dioxins, haloacetic acids) during the bleaching of wood pulp and other fibers used in paper, packaging and molded fiber products including bamboo, *Eucalyptus*, wheat straw, rice and other plant-based sources. For example, bleaching softwood pulp with the peracetate oxidant produces about ten times less total organic halides (TOX) than chlorine dioxide and about 2.5 times less TOX than peracetic acid. Bleaching with the peracetate oxidant can reduce pollution from chemical bleaching of fibers and minimizes toxic byproduct content in chemically bleached paper and molded fiber products such as those used for food packaging and compostable products.

The ability to mitigate microbes that have developed resistance to biocides is a growing challenge. Changing the biocide type periodically is one method used to mitigate microbes that have developed resistance to a particular biocide. This approach is often used in managing microbial populations in cooling tower water and other industrial water applications. However, resistance to multiple forms of chlorine and bromine has created problems with virulent pathogens that are increasingly resistant to antibiotics.

The peracetate oxidant solution provides several different oxidant species in a single solution including the peracetate parent oxidant and several daughter products formed in-situ including singlet oxygen, hydroperoxyl radical, superoxide radical and combined forms that impart high oxidative-reductive potentials (ORP) that are desirable for and correlated with effective microbial control. The combination of multiple oxidant species along with a high ORP can help mitigate resistance of microbes to disinfectants.

The presence of ROS or other reactive species in the formulations herein may in some cases be directly detected and it may be possible to determine the concentrations of certain reactive species (e.g., using spectroscopic methods). However, in some embodiment, in formulations herein the presence of reactive species may only be indirectly demonstrated by measurement of changing properties of the formulation (e.g., ORP measurements or pH change, by changes in concentration of precursors (e.g., rate of peroxyacetic acid concentration decline) or by changes in reactivity of the formulation (e.g., the rate of oxidation of dyes (bleaching rate)) or the rate or occurrence of oxidation of certain species (e.g., polysaccharide breakdown)).

The oxidative reductive potential (ORP) is a measure of how oxidizing or reducing a solution is relative to a standard reference potential measured in volts. Standard reference potentials are measured relative to the hydrogen/hydrogen ion reduction-oxidation potential of V at unit activity for the standard hydrogen electrode (SHE). Generally, solutions with potentials greater than 0 V vs SHE are considered oxidizing (electron accepting) while solutions with potentials less than 0 V vs SHE are considered reducing (electron donating). The measured ORP of water is influenced by its pH or hydrogen ion activity. As the hydrogen ion activity (e.g., concentration, temperature) increases, the ORP of water increases to more positive values. ORP is also influenced by the presence of reducing or oxidizing agents relative to their standard reduction-oxidation potentials and solution activities. ORP is used as a general measure of the antimicrobial strength of a solution containing an oxidizing antimicrobial agent, biocide or disinfectant. ORP may be correlated to relative oxidant concentration for lower oxidant concentrations at constant pH and temperature. This feature is the basis for ORP monitoring systems sometimes used in water treatment and disinfection processes where oxidant dose may be adjusted to maintain a desired ORP and corresponding biocidal activity for a particular oxidant. In some embodiments, the reactive oxygen species formulations may be used in various applications as oxidants and/or biocides. As described herein, different formulations, as assessed by ORP measurement and dye oxidation rate among other properties, may exhibit enhanced activity as a chemical oxidant or as a disinfectant, antimicrobial or biocide. In some embodiments, uses of the reactive oxygen species formulations are provided herein for various industrial or domestic oxidation, clean up and disinfection applications.

More specific applications include without limitation, water treatment and reuse; produced water treatment, process water cleaning and reuse, waste water treatment, greywater, raw water, ground water, tailing pond water, refinery waste water, cooling tower cleaning, cleaning/disinfections of water wells, pipes and containers, textile dye recycle and waste water treatment, pulp and paper processing waste water treatment and recycle, specialty bleaching applications, and non-potable water systems.

In water treatment processes, the chlorine-free and bromine-free reactive oxygen species formulations may be used to provide treatment without formation of undesired chlorinated or brominated byproducts. In water treatment processes, the chlorine-free and bromine-free active oxygen species formulations may be used to provide treatment in the absence of chlorine, chlorine dioxide and/or ozone. For applications of the formulations herein the formulation is contacted with a substrate or environment to be oxidized or treated. Any means of contacting may be employed, that is suitable for retention of the oxidation activity of the formulation and that is suitable for the environment and/or substrate. Formulations are liquid and may be employed in a concentrated form or a diluted form. Formulations may be diluted, if desired, before, during or after initial contact. The concentration of formulations in contact with an environment and/or substrate may be varied during contact.

A given application may employ separate contacting events which may be the same or different and which may employ the same formulation or precursor formulation. A given application may employ contact with more than one formulation or precursor thereof. The environment and/or substrate may, for example, be contacted with an activated liquid formulation containing reactive oxygen species. Alternatively, the environment and/or substrate may be contacted with a liquid precursor formulation that will generate reactive oxygen species on activation and the formulation is activated as or after it comes into contact with the environment or substrate.

For example, the environment or substrate may itself provide for activation, such as providing acidity that affects ROS formation rates and changes in oxidant speciation, fragmentation behavior or reactivity caused by acid-base equilibria. One or more additional steps of activation to form additional reactive species may occur after the contact of the formulation or the precursor formulation with the environment and/or substrate. For example, redox active materials or charged materials including transition metal species, unsaturated organic materials, sulfides and suspended solids can interact with and react with the parent peracetate oxidant to initiate fragmentation of the parent peracetate oxidant leading to the formation of ROS. Thermal activation can also be used to increase the formation rate of ROS, increase the fragmentation rate of the peracetate and increase overall peracetate oxidant solution's antimicrobial activity, bleaching power and reactivity with impurities or substrates. Irradiation of peracetate-containing solutions with ultraviolet light may also be used to promote activation. Contact with the environment or substrate may be controlled by addition of a selected volume or concentration of formulation or its precursor to the environment or in contact with the substrate. Alternatively, contact may occur by addition, including controlled addition of the substrate to the formulation or a precursor thereof.

Contact may be combined with stirring or other agitation, with scrubbing, scraping or other abrasive method if appropriate for the environment and/or substrate. Contact may be combined with removal precipitant or other solids present or formed in the environment or on contact with the substrate. The environment or substrate may be pre-treated prior to contact. The treated environment to substrate may be subject to another form of cleaning or disinfection.

Water system equipment is serviced to remove bacterial growth, biofilm, slime buildup, mineral scale deposits, corrosion and contamination. These issues are common among, waste water, greywater, raw water, ground water, tailing pond water, refinery waste water, produced water, various industrial and food processing waters, water recycling loops, pulp and paper mills, cooling towers and water loops, and non-potable water systems. Microbial control, removal of slime (the decaying remains of dead bacteria and other organic materials), microbial corrosion control and scale removal are significant maintenance issues for prolonging the production capacity and lifetime these systems. Pipelines, tanks and other equipment carrying raw water, wastewater, produced water, greywater and other untreated water will encounter microbial growth and slime formation and will require cleaning.

Microbial control in water is imperative to a wide variety of processing and manufacturing systems. These systems can include water recycling loops, pulp and paper mills, cooling towers and water loops, and non-potable water systems. Treatment of water for microbial control in water recycle loops is critical for maintaining efficient processes, protecting equipment from biofouling and biocorrosion, preventing contamination of products, reducing downtime and protecting the health of people exposed to such processes and products. Furthermore, microbial control in water recycle loops also provides odor control by minimizing fermentation, hydrogen sulfide production and algal decomposition. Microbial control in pulp and paper mills serves to protect the integrity of pulp slurries, coating ingredients, whitewater loop, process equipment, and paper quality. Controlling sessile bacteria helps to prevent the accumulation of biofilm deposits which cause microbiologically influenced corrosion (i.e., biocorrosion). Slime deposits are often a combination of bacteria and fungi. Importantly, when biofilms and their detritus detach from surfaces in the wet end papermaking process, they can cause holes and other defects in finished paper products. Therefore, preventing biofilm growth helps to avoid such defects. Microbial control in cooling towers and cooling water loops serves to improve cooling efficiency, minimize microbiologically influenced corrosion, control odors, prevent clogging of pumps and pipes, reduce microbial loading in blowdown, and minimize microbial exposure of surrounding areas from drift. Microbial control may also occur on surfaces serving to bleach, sanitize and/or disinfect the surfaces of a processing or manufacturing system. Microbial control targets include aerobic and anaerobic bacteria (slime formers, acid producers, metal depositors, nitrobacteria, sulfate reducers, nitrate reducers), fungi, algae, molds, and yeast. Some bacteria are pathogenic, for example, *Legionella pneumophila*, which poses health risks. Some algae, such as cyanobacteria, produce algal toxins that pose potential health hazards.

Biocides used for microbial control need to be effective and efficient at neutral and alkaline pH. They also need to be effective at elevated levels of suspended solids (including silt, pulp, fillers, pigments, suspended metals, oils, polymers) and dissolved solids (including salt, scaling minerals, carbonate, dissolved metals, scale inhibitors and other additives that may be encountered in various processes). Oxidizing biocides are a fast-acting line of defense and represent a significant expense in operations. Oxidizing biocides should be very active and have a limited lifetime with no reactive residuals so that they do not interfere with non-oxidizing biocide chemicals used to provide longer-term biostatic conditions.

Another embodiment is the ability to combine the use of peracetate oxidant solution and chlorine bleach for improved antimicrobial treatment of water. When a highly impaired water is treated with peracetate oxidant solution the ORP can be increased to, for example, about 600-700 mV vs SHE, which is a reasonable level for microbial disinfection. Treating the same water with a comparable dose of bleach can increase the ORP to a similar mV range, which is also a reasonable level for disinfection. When the bleach treatment is added on top of the peracetate oxidant treatment the ORP can be increased to over 800 mV, which indicates that there is an additive oxidative effect that increases the oxidation potential of the water and the corresponding level of antimicrobial treatment. This additive behavior between oxidants is in contrast to the typical consumptive reaction between peroxide-based oxidants and chlorine bleach. For example, combining hydrogen peroxide treatment with chlorine bleach treatment results in the consumptive reaction between bleach and hydrogen peroxide and a net loss of oxidants.

Similarly, combining peracetic acid treatment with chlorine bleach treatment results in reaction between bleach and the hydrogen peroxide contained in the peracetic acid solution (e.g., 15% peracetic acid solution can contain 10-25% hydrogen peroxide) resulting in a net loss of oxidants. In addition, the alkalinity of chlorine bleach (sodium hypochlorite in sodium hydroxide solution) can accelerate the consumptive reaction between peracetic acid and hydrogen peroxide when diluted into a water stream of neutral to slightly alkaline pH (peracetic acid is ionized by alkalinity and then reacts with hydrogen peroxide).

In some embodiments, peracetate oxidant solution showed an unexpected, rapid thermal activation behavior at pH 8.5 and 50° C. in clean water conditions. To test this behavior without competing contributions from impurities the peracetate oxidant concentrate was added to distilled water pre-heated to 50° C. After the solution pH naturally decreased from 10 to 8.5 it was maintained at pH 8.5 throughout the remainder of the test by adding 4 M sodium hydroxide as needed. The concentration of peracetate oxidant decreased over time with an accompanying increase in ORP to over 700 mV vs SHE within 40 minutes. The decrease in peracetate concentration and increase in ORP was significantly faster at 50° C. than that previously observed at room temperature in clean water conditions. The peracetate consumption and ORP behavior suggests that one or more intermolecular reactions is occurring between molecules and/or reactive oxygen species generated in-situ at the expense of peracetate. The products of these reactions generate a composition with meta-stable species that exhibit a high ORP. In contrast, the same test with peracetic acid showed stable peracetic acid and hydrogen peroxide concentrations for about 90 minutes and the ORP was constant around 280 mV vs SHE.

In some embodiments, microbial control in water at slightly alkaline pH was compared between peracetate oxidant, chlorine bleach, peracetic acid and chlorine dioxide. Alkaline pH is encountered in a variety of applications where microbial control and sanitization is needed, including pulp and paper processing, cooling towers, water treatment and chill tanks in poultry processing. Some oxidants are less effective at sanitizing at alkaline pH such as chlorine bleach (hypochlorite) at a pH above its pKa of 7.5. Peracetate oxidant and chlorine dioxide performed well as antimicrobial disinfectants at slightly alkaline pH compared to peracetic acid and chlorine bleach, which had the lowest performance.

Referring now to an exemplary paper mill processing system 370 as shown in FIG. 1 for illustrative purposes only, typically chlorine bleach is used to control microbial growth in printing paper in stock preparation and white water recovery. Pulp stock or fiber furnish 301 is pumped into the blend chest 305 where chemical additives 303 may be added, such as dyes. A blend of pulp types (hardwood and softwood) may be added and combined. Re-processed fiber and broke pumped from the broke chest 300 are also combined in the blend chest 305. The thick stock made in the blend chest 305 is transferred to the machine chest 310 where the consistency is leveled during a short retention time. The thick stock is then transferred to the wire pit 315 for dilution to the head box consistency. The diluted stock then passes through a cleaner bank 320 to remove unwanted solids and then to a deaerator 325 to separate entrained gas from the stock. After passing through a final screening 330 the diluted stock is fed into the head box 335. From the head box 335 the stock is fed to the former or wires 340 for sheet forming. Suction boxes under the wire remove bulk water from the sheet and this water is sent to the white water chest 345. The sheet then passes through a series of heated drying rollers and pressing rollers to produce the finished paper sheet 360. The white water is sent through a cleaning device 355, such as a centrifuge, to separate and recover fibers before the water returns to the wire pit 315 for stock dilution. Trimmings and loose fiber are collected from the former 340, pressing and drying 350 stages and sent to the broke chest 300. The broke is processed into dispersed fiber and returned to the blend chest 300. Each stage in the paper mill, and every surface in that stage, is contaminated with microbes and requires periodic cleaning to maintain consistent paper quality. Two locations for chlorine bleach addition for microbial control in the white water 345 and broke chests 300 are shown.

Compounds for microbial control in system 370 can be injected at multiple points throughout the system. Exemplary, but by no means limiting injection points illustrated in FIG. 1 include:
 a. Injection point E: at the white water chest; and
 b. Injection point F: at the broke chest.

In one embodiment, peracetate oxidant solution is added to at least one of the injection points E and F at injection. The peracetate oxidant solution could replace or be used in conjunction with chlorine bleach or other common bleaching compounds. Peracetate oxidant injection at Injection points E and F results in improved efficiency of oxidant mixing, contact and water treatment.

In some embodiments, sodium peracetate oxidant solution is used to control microbial growth in a printing paper mill in stock preparation and white water recovery. White water entrains fiber, chemicals and microbes from the paper web. Microbes have an opportunity to propagate during extended residence time in the white water chest. Pulp sources entering the machine chest, such as boke and recovered fiber, will carry elevated microbial loads after their recovery form the paper machine process. Microbial concentrations can exceed $10^6$ to $10^7$ cells/mL, a level that reduces paper quality, accelerates biofilm growth and microbially influenced corrosion, increases paper defects and odor problems. These problems increase the frequency of down time for maintenance and increase paper reject.

Several points exist where the peracetate oxidant solution can be added to the paper mill process. Ideally the peracetate solution is added to a fluid (water and pulp) where there is a contact time of several minutes to allow for more effective microbial control in the presence of high solids and allowing for thermal activation of the peracetate in warm and hot water streams that are typical in a paper mill. The use of peracetate oxidant has virtually no impact on pH, thereby avoiding the use of a second chemical feed for pH balance as is necessary when using moderate concentrations of acidic oxidants like chlorine dioxide and peracetic acid in a closed or partially closed-loop system.

In some embodiments, the peracetate oxidant solution is shown to be efficient for the bleaching of Kraft pulp and its performance approaches that of chlorine dioxide. The preferred pH for bleaching with peracetate oxidant solution is about pH 8 to about pH 12 where the ROS content and activity is greatly enhanced at elevated temperatures. Pulp bleaching is very slow at room temperature (takes more than 1 hour to achieve modest bleaching) but is very rapid at 50° C. (30 minutes to achieve significant bleaching). For comparison, the most efficient pH for bleaching with peracetic acid is at pH 7 and lower, however it is not as efficient as peracetate oxidant overall and does not show thermal activation for the production of ROS. Using peracetate oxidant in pH neutral to alkaline bleaching conditions has very little impact on alkali consumption in the bleaching process. In contrast, pH neutral to alkaline bleaching with chlorine dioxide or peracetic acid consumes large quantities of alkali to neutralize the acidity in these oxidants as alkali is caustic soda.

In some embodiments, production of chemicals and fuels from bio-based, renewable feedstocks is achieved by fermentation or transformation with engineered microbes including yeasts, bacteria and enzymes. The engineered microbes can be rapidly contaminated and overwhelmed by wild strains present in the feedstock materials unless the feedstocks are disinfected prior to their addition to a fermenter or bioreactor. There are a wide variety of feedstocks being utilized in bio-based chemical production including, for example, natural polysaccharide materials (guar and xanthan gums, lignin), sugars (corn, cane, beet, sorghum, wheat and tapioca), fats, fatty acids, glycerin, corn stover, mechanically pulped trees and switchgrass. Feedstocks are often disinfected or sterilized under autoclave conditions, high pressure steam at 121° C., to avoid introducing chemistry that would degrade feedstock or product quality such as halogen-based oxidizing biocides and ozone. However, autoclave treatment has high energy and equipment costs and is an excessive microbial control method for chemical and fuel production.

Figure 2:
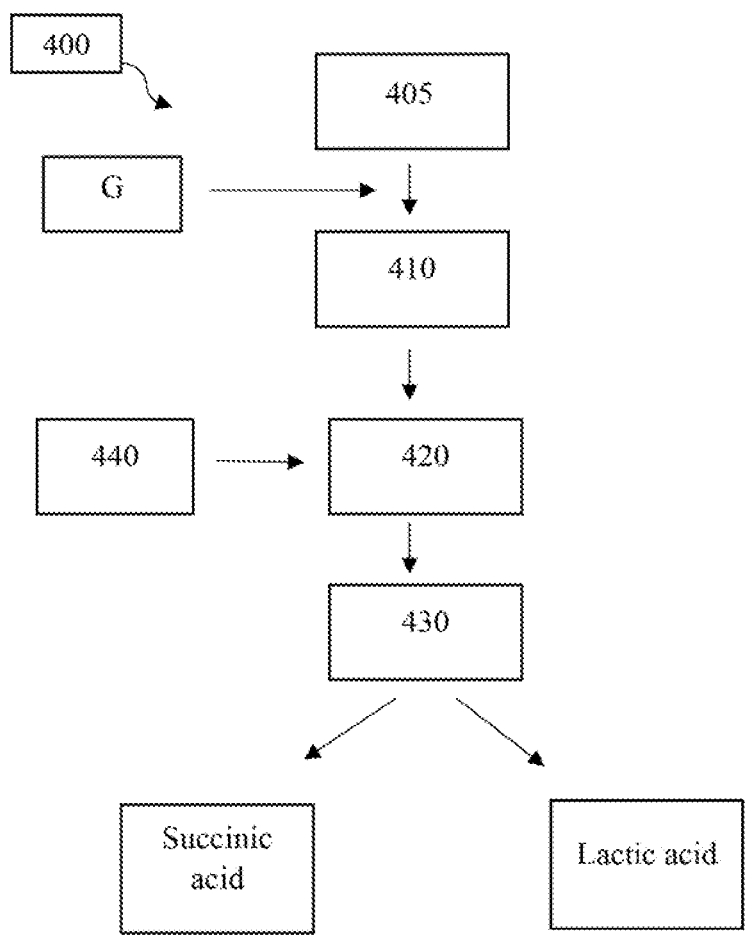
FIG. 2 is a simplified schematic diagram of an embodiment of a feedstock processing system.

Referring now to an exemplary feedstock processing system 400 as shown in FIG. 2 for illustrative purposes only using high pressure steam, feedstock material 405 is placed in a heated blending tank 410 and mixed, the material is then fed to a fermenter 420 along with nutrients, pH buffers or additives 440 necessary for fermentation process. Following fermentation chemical products 430 are recovered and are separated into succinic acid and lactic acid.

Compounds for microbial control in system 400 can be injected at multiple points throughout the system. Exemplary, but by no means limiting injection points illustrated in FIG. 2 include:

Injection point G: before the blending tank.

In one embodiment, peracetate oxidant solution is added to at least one of the injection point G at injection. The peracetate oxidant solution could replace or be used in conjunction with autoclave conditions.

In some embodiments, peracetate oxidant solution is used for microbial disinfection of polysaccharide feedstock materials used for producing succinic acid and lactic acid in a fermentation process. The peracetate is blended with the feedstock mixture in a blending tank to make an initial sodium peracetate concentration of up to about 130 ppm (by weight) and this mixture is heated to around its fermentation temperature of about 50-60° C. In this temperature range thermal activation of the peracetate oxidant occurs which increases antimicrobial activity and the rate of oxidant consumption such that the treatment is more rapidly finished and active oxidant is eliminated before entering the fermentation stage containing the engineered microbes.

For example, a guar gum dispersion in water was tested for microbial disinfection and preservation with sodium peracetate solution. Guar gum dispersions were made in 150 mL glass jars with air tight covers by dissolving/dispersing 0.60 grams of food grade guar gum in 60 mL of distilled water containing 0.60 g of sodium chloride to make 1% guar dispersions. The dispersions were heated in a water bath to 30° C. for 45 minutes to hydrate the guar. A first jar sample was cooled to room temperature and held as the control sample. The viscosity of the room temperature guar dispersion was similar to warm honey. A second jar sample was spiked with about 130 mg/L dose of sodium peracetate and mixed thoroughly. The temperature was maintained at 30° C. for 60 minutes and then cooled to room temperature. The viscosity of the second sample appeared very similar to the first. Within 24 hours of preparation the first, control sample had a significant loss of viscosity while the second, treated sample remained visibly unchanged. After seven days the first, control sample had microbial growth visible as a biofilm developing on the surface of the liquid while the second, treated sample remained visibly unchanged.

In some embodiments, peracetate oxidant solution is used for sanitization. The sanitization of equipment used for food, beverage and dairy processing and the sanitization of packaging, bottles and containers for packaging of these products is critical for protecting consumers from illness, prevent spoilage, increase shelf life, and maintain clean equipment and facilities. Common methods of sanitizing equipment surfaces is conducted by soaking, spraying and clean in place (CIP) processes. CIP processes involve the preparation of cleansers and sanitizer solutions in day tanks (often in 50-500 gallon volumes) and dispensing them into pipes, tanks and other processing equipment that is not disassembled for cleaning.

Chemical cleansers and sanitizers are used where hot water sanitization at high temperature (at least 77° C.) is not practical or damaging to equipment and where other contaminants (e.g., organic materials, mineral scale, stains) also need to be removed. Alkaline oxidizing cleanser solutions are particularly effective at removing protein soils, oils, fat deposits and killing microbes compared to alkali detergents alone. Acidic oxidizing cleansers are effective at removing mineral scale, milkstone, iron and killing microbes.

The heating of sanitizing solutions (e.g., hypochlorite, chlorine dioxide, iodine, peracetic acid) to modest temperatures (typically 40-60° C.) is a common practice to improve the effectiveness of a disinfectant. This is partly based on the principles that diffusion rates and chemical reaction rates increase with increasing temperature and that surface tension decreases thereby improving surface wetting and interaction with microbial deposits. The peracetate oxidant solution has the additional benefit over conventional oxidizing biocides of being thermally activated to produce multiple germicidal reactive oxygen species more rapidly, which significantly accelerates and increases the oxidant solution's sanitizing power. The peracetate oxidant performs well at alkaline pH making it effective for alkaline oxidizing cleanser solutions with strong germicidal activity.

Hypochlorite is problematic in heated sanitizing solutions due to its corrosivity to stainless steel, particularly aggressive pit corrosion. For example, the warranty of a stainless steel cleanser system or CIP system is voided if the chlorine concentration exceeds 80 mg/L, at 40° C. The presence of chloride ion also enhances the corrosion of stainless steel at elevated temperatures. Chlorine is also volatile and off-gasses rapidly from warm cleanser solutions.

Peracetate oxidant solution is compatible with stainless steel and has a very low corrosion rate on copper. It has low volatility allowing it to remain in solution at elevated temperatures for improved efficiency and eliminates exposure of personnel to chlorine or chlorine dioxide vapors. Peracetate oxidant has very low halogenated byproduct formation potential making it safer for cleaning and sanitizing food contact surfaces (no toxic halogenated residues) and preventing discharge of halogenated oxidation and disinfection byproducts. Because of these attributes peracetate oxidant can be safely used in higher concentrations than hypochlorite, chlorine dioxide and ozone for sanitization.

In some embodiments, transport and storage of peracetate oxidant solutions is avoided by its generation from stable feedstocks at or near the point of use. The small amount of peracetate present on site is produced in water at dilute concentrations (less than 8%) thereby avoiding hazards associated with highly concentrated or pure oxidant materials and minimizing fugitive air emissions and worker exposure to harmful materials, VOCs or nuisance odors. Potential fugitive air emissions from the peracetate oxidant solution production process are a small amount of water vapor and oxygen gas. The produced peracetate oxidant solution concentrate is dispensed by means of a pump, eductor or other engineered conveyance device that transfers the liquid product in a contained system to the point of use. The peracetate oxidant solution is produced as needed on site and on demand thereby eliminating storage and handling of large quantities of the oxidant product material on site.

In some embodiments, peracetate oxidant solutions have the ability to reduce corrosion in pulp and paper mills serving to protect the integrity of pulp slurries, coating ingredients, whitewater loop, broke processing system, process equipment, and paper quality. Controlling sessile bacteria helps to prevent the accumulation of biofilm deposits which cause microbiologically influenced corrosion (i.e., biocorrosion). Slime deposits are often a combination of bacteria and fungi. Importantly, when biofilms and their detritus detach from surfaces in the wet end papermaking process, they can cause holes and other defects in finished paper products. Therefore, preventing biofilm growth helps to avoid such defects.

In some embodiments, peracetate oxidant solution is less corrosive than commonly used oxidizing biocides (chlorine, chlorine dioxide), especially when the biocides come in contact with various process materials such as steel, copper and brass alloys. Oxidizing biocides used in processes where elevated temperatures and turbulence are present in the liquid phase should ideally have low vapor pressures to minimize oxidant loss to evaporation and vapor phase corrosion of surrounding equipment and structures. It is important to consider corrosion rates of materials like metal alloys under various oxidant use conditions including shock treatments and bleaching at high concentrations, water treatment at lower concentrations and vapor corrosion in the head space above oxidant solutions.

In some embodiments, corrosion conditions evaluated were relevant to shock treatment in pipes and well casings. Steel alloy was tested as a common pipe and well casing steel with resistance to hydrogen sulfide corrosion and is used in the oilfield. Copper coupons were tested as a common material used in heat exchangers in cooling towers and water cooling loops. Side-by-side corrosion tests using different oxidants (peracetate oxidant solution, chlorine dioxide and chlorine bleach) under the same test conditions demonstrated significantly reduced corrosion rates for the peracetate solutions compared to the other oxidants tested. Shock treatment corrosion tests were conducted over a period of 24 hours without replenishing oxidant. These conditions were conducted to simulate a single, elevated oxidant dose applied in a shock treatment program. The duration of the shock treatment is expected to be limited in time by the rate of oxidant consumption, which is expected to be less than 24 hours in highly contaminated and elevated temperature conditions.

Corrosion rates for chlorine dioxide were 4 to 6.5 greater than for peracetate oxidant on steel. Coupons exposed to chlorine dioxide developed a red-orange colored iron oxide coating with moderate to severe blistering and flaking. Salt water conditions did not significantly influence corrosion rate or appearance. Elevated temperature increased the peracetate oxidant corrosion rate by about 1.5 times. Chlorine dioxide corrosion decreased slightly at higher temperature, which may have been due to faster oxidant loss from outgassing or due to a heavier oxide scale formation that partially inhibited the corrosion rate.

In some embodiments, water treatment corrosion test conditions similar to those found in water treatment facilities, cooling towers and pulp & paper mills were conducted on a common pipe steel and copper to compare continuous exposure to lower concentrations of peracetate oxidant, chlorine dioxide, and chlorine bleach. Saturated oxygen from air was used as the control test for the corrosion rate of just the carrier fluid (water) in air. The peracetate oxidant was the least corrosive with rates only slightly higher than dissolved oxygen. Oxidant concentration was monitored hourly and additional oxidant was added to the carrier fluid during the test period as needed.

On steel the corrosion rate of chlorine dioxide was 1.7 to 2.1 times greater than peracetate oxidant and chlorine bleach was up to 1.5 times more corrosive than peracetate oxidant at room temperature. Increasing temperature to 140° F. increased corrosion rate of peracetate oxidant about 1.6 times while the chlorine dioxide corrosion rate doubled and the peracetic acid corrosion rate quadrupled.

On copper, chlorine dioxide was 12 times more corrosive than peracetate oxidant and bleach was 440 times more corrosive at 140° F. Corrosion of copper by peracetate oxidant was inhibited relative to oxygen in air, likely due to better passivation of the copper surface with a tighter oxide layer formed by peracetate oxidant. Bleach and chlorine dioxide tarnished the copper coupons with a green-black oxide layer while coupons in peracetate oxidant remained bright and untarnished.

In some embodiments, vapor corrosion tests reflecting vapor corrosion conditions potentially encountered in hot environments such as the vapor head space in closed tanks and pipes and in open-air paper making processes and their facilities were also conducted. Vapor corrosion is a particular problem in paper mills and cooling towers where structural steel supports and other equipment is degraded and must be replaced periodically. These tests compare continuous exposure to vapor-phase concentrations of peracetate oxidant, chlorine bleach, chlorine dioxide and peracetic acid in the head space above oxidant solutions in sealed containers. Saturated oxygen from air was used as a control test for the corrosion rate of just the carrier fluid in air. Measured corrosion rates in the vapor phase are reduced significantly using peracetate oxidant relative to bleach, chlorine dioxide and peracetic acid. The low volatility of peracetate oxidant solution (peracetate oxidant is a solid in its native form) minimizes vapor corrosion and odors from the oxidant. This behavior is in contrast to elemental chlorine, chlorine dioxide and ozone, which are gasses with very limited solubility in water at elevated temperatures, and peracetic acid, which is significantly volatile.

Vapor corrosion tests were conducted with test coupons suspended in the vapor head space in closed containers over a period of 6 hours, which was long enough to provide accurate weight loss measurements while monitoring oxidant concentration. Oxidant concentration was monitored hourly and additional oxidant was added to the carrier fluid during the test period as needed. On steel the peracetate oxidant was about 1.7 times more corrosive than air, chlorine bleach was about 8.6 times more corrosive than air, chlorine dioxide was about 11 times more corrosive than air and peracetic acid was about 5 times more corrosive than air (peracetic acid consisted of a 1:1.3 mass ratio of PAA to $H_2O_2$ in acetic acid and water).

In some embodiments, tests were conducted to evaluate the formation potential of halogenated organic oxidation byproducts with peracetate oxidant relative to other common oxidants (peracetic acid, chlorine bleach, chlorine dioxide) and a blank (no oxidant). Treatment of flowback water from a hydraulically fractured oil well and bleaching of wood pulp were conducted as test cases. Water samples were tested for total organic halide (TOX) after water treatment and bleaching processes. There was no detectable TOX formation in the treated flowback water and significantly reduced TOX formation during pulp delignification and bleaching.

In some embodiments, peracetate oxidant solution was tested for its propensity to form bromate in water containing high bromide ion concentrations that are encountered in seawater, formation water and waste water. No bromate formation was detected in the treatment of a simulated seawater composition and a production water from the oilfield under conditions that are favorable for bromate formation. In contrast, bromate formation as an oxidation byproduct is a well-known issue for oxidants such as ozone and peracetic acid.

EXAMPLES

Having now described the invention, the same will be more readily understood through reference to the following example(s), which are provided by way of illustration, and are not intended to be limiting of the present invention.

Example 1: Paper Mill Treatment

Sodium peracetate oxidant solution is used to control microbial growth in a printing paper mill in stock preparation and white water recovery. White water entrains fiber, chemicals and microbes from the paper web. Microbes have an opportunity to propagate during extended residence time in the white water chest. Pulp sources entering the machine chest, such as boke and recovered fiber, will carry elevated microbial loads after their recovery form the paper machine process. Microbial concentrations can exceed $10^6$ to $10^7$ cells/mL, a level that reduces paper quality, accelerates biofilm growth and microbially influenced corrosion, increases paper defects and odor problems. These problems increase the frequency of down time for maintenance and increase paper reject.

Several points exist where the peracetate oxidant solution can be added to the paper mill process. Ideally the peracetate solution is added to a fluid (water and pulp) where there is a contact time of several minutes to allow for more effective microbial control in the presence of high solids and allowing for thermal activation of the peracetate in warm and hot water streams that are typical in a paper mill. The use of peracetate oxidant has virtually no impact on pH, thereby avoiding the use of a second chemical feed for pH balance as is necessary when using moderate concentrations of acidic oxidants like chlorine dioxide and peracetic acid in a closed or partially closed-loop system.

A first peracetate oxidant dose point is associated with the white water recovery. Peracetate oxidant is dosed into the inflow of the white water chest at about 20-40 ppm concentration relative to the inflow fluid volume rate. For example, a 10,000 gpm inflow rate would be injected with 8 gpm of a 5% sodium peracetate solution to provide a 40 ppm oxidant dose concentration. This amount of oxidant can provide up to about a 6 log reduction in microbial concentration depending the type and concentration of paper solids, additives, impurities and microbial species present. When the recovered white water reaches the wire pit it can potentially contain an oxidant residual when it is combined with the thick stock. If no oxidant residual is required at the wire pit due to a sensitive dye or other additive in the thick stock the amount of peracetate oxidant added to the white water can be reduced.

A second peracetate oxidant dose point is associated with the broke chest. Peracetate oxidant is dosed into the inflow of the broke tank at about 40-60 ppm concentration relative to the inflow fluid volume rate. This amount of oxidant can provide up to about a 6 log reduction in microbial concentration depending on temperature and the type and concentration of paper solids, impurities and microbial species present. When the broke reaches the blend chest it can contain an oxidant residual. If no oxidant residual is required at the blend chest the amount of peracetate oxidant added in the broke chest can be reduced.

Using the peracetate oxidant as a biocide in a paper mill process reduces the vapor corrosion rate of an oxidizing biocide to nearly the rate of air on steel around the paper machine. The loss of peracetate to evaporation is very low, which also results in greater use efficiency and reduced exposure of personnel to nuisance vapors relative to chlorine, chlorine dioxide or peracetic acid products.

Using peracetate oxidant as a biocide in producing paper grades for food packaging and totally chlorine free (TCF) paper provides unexpected advantages of imparting no odor to the paper and producing little to no halogenated byproducts.

Example 2: Disinfection of Feedstocks for Bio-Based Chemical Production

Sodium peracetate oxidant was used for microbial disinfection of polysaccharide feedstock materials used for producing succinic acid and lactic acid in a fermentation process. The peracetate is blended with the feedstock mixture in a blending tank to make an initial sodium peracetate concentration of up to about 130 ppm (by weight) and this mixture is heated to around its fermentation temperature of about 50-60° C. In this temperature range thermal activation of the peracetate oxidant occurs which increases antimicrobial activity and the rate of oxidant consumption such that the treatment is more rapidly finished and oxidant residual is eliminated before entering the fermentation stage containing the engineered microbes.

The thermally activated peracetate disinfection treatment is conducted for 30 to 90 minutes depending on the oxidant consumption rate, solids loading and particle size of the feedstock materials. The level of residual active oxidant can be monitored by ORP or by a peroxide titration method. The ORP of the active oxidant mixture can exceed 700 mV (vs SHE) during treatment while the ORP will drop significantly when the oxidant has been consumed, for example, to less than 500 mV.

After antimicrobial treatment the feedstock materials are fed to the fermenter along with other nutrients, pH buffers or additives necessary to support the fermentation process. The byproducts of the peracetate formulation, including acetate and glycerol, are readily fermented in the fermentation process and do not need to be washed or separated from the disinfected feedstock materials. After fermentation the chemical products (succinic and lactic acid) are separated from the fermentation broth, refined and purified.

Example 3: Bleaching of Kraft Pulp

Side by side bleaching tests were conducted to compare the relative bleaching rate and efficiency of peracetate oxidant solution with peracetic acid and chlorine dioxide under relatively mild pulp bleaching conditions. Sodium hydroxide (ACS reagent grade), glacial acetic acid (certified ACS), 98% sulfuric acid (ACS reagent grade), 3% hydrogen peroxide (topical solution), 35% hydrogen peroxide (stabilized, Acros) ceric sulfate standard solution, 0.1 N (Fisher), sodium thiosulfate standard solution, 0.025N (HACH) and ammonium molybdate reagent (HACH) were used as received.

Sodium peracetate oxidant solution was produced by combining 7.0 mL of 3% hydrogen peroxide with 1.0 mL of distilled water, 6.5 mL of 1 molar sodium hydroxide and 0.81 mL of triacetin. The mixture was rapidly stirred and allowed to react for about 2 minutes at room temperature making a 3.7% wt/vol concentration of sodium peracetate. The sodium peracetate concentration was measured using the HACH iodometric titration method for hydrogen peroxide and adjusting for molecular weight.

A peracetic acid stock solution containing about 11-16% peracetic acid and 15-22% hydrogen peroxide was prepared by combining 20 mL of cold 35% hydrogen peroxide into 30 mL of cold glacial acetic acid. The mixture was allowed to equilibrate at room temperature in a vented container away from light for 4 days and then refrigerated for storage of up to two weeks. The actual peracetic acid and hydrogen peroxide concentrations were measured before use by the determination of hydrogen peroxide and peracetic acid in solutions method of Enviro Tech Chemical Services which incorporates titration of hydrogen peroxide with ceric sulfate and ferroin indicator followed by titration of peracetic acid with sodium thiosulfate and potassium iodide indicator.

Chlorine dioxide stock solution preparation: One AQUA-Tab 20 G chlorine dioxide tablet (Beckart Environmental, Inc.) was dissolved in 27 oz (800 mL) of distilled water in a closed polyethylene container according to the product instructions to produce up to a 0.3% solution. The yellow solution was allowed to sit for at least 1 hour before use and stored in a refrigerator. The chlorine dioxide concentration was measured prior to use by the HACH DPD method and DR900 colorimeter. Chlorine bleach (5%, Great Value brand) was measured for total chlorine concentration prior to use by the HACH DPD method and DR900 colorimeter.

Solution pH was measured using a high sodium pH electrode (Oakton) with three point calibration. ORP was measured using a platinum electrode ORP probe (Oakton) calibrated with an ORP standard (420±3 mV vs SHE, Orion 967901, Thermo Fisher). ATP (adenosine triphosphate) concentration was measured using the LuminUltra 2nd Generation metabolic ATP measurement technology with the LuminUltra™ Quench Gone-Organic Modified sampling method, a PhotonMaster Luminometer™ and LumiCalc™ software. Acid producing bacteria (ABP) and sulfate reducing bacteria (SRB) cell culture concentrations were measured with standard 1 mL serial dilutions using Intertek APB and SRB culture media, 6% salinity.

Kraft pulp was prepared from 50 lb Kraft paper (Pacon Corp.) by blending cut paper pieces in distilled water in a blender for 30-45 seconds to disperse the fibers. The pulp was drained over a screen, spread on a clean surface and air dried (ambient air less than 25% relative humidity at 20° C.) until a stable weight was obtained.

Bleaching and hand sheet casting was conducted by the following procedure. A 3.75 g portion of the dried pulp was pre-wetted in about 75 mL of distilled water. The wetted pulp was then transferred to a small blender jar and blended for 10 seconds to disperse fiber clumps and the pulp slurry was transferred to a beaker with magnetic stir bar and known volume of water. The slurry was heated in a temperature controlled water bath positioned over a magnetic stir plate. The pH of the pulp slurry was adjusted to the desired level with 4 normal sodium hydroxide or sulfuric acid solution. A volume of oxidant concentrate and additional water were added to make a 1.5% pulp consistency in a total liquid mass of 250 g. The pulp slurry was stirred throughout the bleaching time. After the bleaching process the slurry was vacuum filtered through a Buchner funnel over a medium porosity filter paper disc having a 9 cm (3.5 inch) diameter. The dewatered hand sheet was peeled off of the filter paper and air dried to a constant weight. Kappa numbers of hand sheets were measured in duplicate following the procedure described in the Mantech Inc. Kappa number determination protocol.

TABLE 3

| Entry No. | Bleach Time (min) | Oxidant | Initial Oxidant Conc. (g/L PAA equiv.) | Initial pH | Final pH | Final ORP (mV vs SHE) | Kappa No. |
|---|---|---|---|---|---|---|---|
| 1 | Unbleached | — | — | — | — | — | 30 |
| 2 | 30 | ClO$_2$ | 1.13 | 8.2 | 6.4 | 896 | 22 |
| 3 | 30 | Peracetate oxidant | 4.0 | 7.1 | 5.3 | 1025 | — |
| 4 | 30 | Peracetate oxidant | 4.0 | 8.1 | 7.1 | 768 | — |
| 5 | 30 | Peracetate oxidant | 4.0 | 8.7 | 7.3 | 690 | 24 |
| 6 | 30 | Peracetate oxidant | 4.0 | 10.0 | 8.5 | 765 | 24 |
| 7 | 30 | PAA* | 4.0 | 7.0 | 7.0 | 502 | 31 |
| 8 | 30 | PAA* | 4.0 | 8.0 | 8.0 | 406 | — |
| 9 | 30 | PAA* | 4.0 | 8.9 | 8.8 | 253 | 29 |

*PAA stock solution was measured as 11.4% PAA and 15.6% H$_2$O$_2$, pH = 1.0

Visible differences in pulp brightness were observed and Kappa number measurements were used to quantify these differences. The initial pulp (a mixture of hard and soft wood) had a Kappa number of 30. Bleaching with peracetic acid is known to be most effective near pH 7-8 with the tradeoff of promoting losses from wasteful side reactions that increase significantly above pH 7. Under the conditions of the hand sheet tests summarized in Table 1 the bleaching efficiency of peracetic acid was poor with only up to one Kappa unit reduction measured. An additional inefficiency was the need to use a large amount of amount of alkali (e.g., sodium hydroxide) to neutralize the acetic acid and peracetic acid content to raise the pH of the bleaching solution to pH 7. For example, 10.9 g/L of sodium hydroxide was needed to adjust the pH of a 4.0 g/L peracetic acid solution up to pH 7.0.

A similar issue of alkali consumption exists for chlorine dioxide, which is strongly acidic. To bleach with 1.0 g/L of chlorine dioxide at pH 8 about 1.5 g/L of sodium hydroxide was consumed, which adds a significant cost in a bleaching process. For example, bleaching with 50 lbs of C102 per ton dry pulp would consume approximately 75 lbs of NaOH per ton dry pulp for acid neutralization.

In contrast, the natural pH of the peracetate oxidant solution when used in pulp bleaching is typically about pH 8 to 9, which falls within its optimal bleaching pH range and does not require the addition of alkali. The bleaching performance of peracetate oxidant appeared the same from pH 8 to pH 11. The bleaching rate and pulp brightness was significantly greater for peracetate oxidant at pH 8-10 over peracetic acid at pH 7-9. Only chlorine dioxide achieved a greater brightness and lower Kappa number in the same time period and pH range. However, chlorine dioxide gas was rapidly volatilized from the warm bleaching slurry while the peracetate oxidant primarily remained in solution. Peracetic acid produced a strong odor of acetic acid and peracetic acid being volatilized from the warm bleaching slurries and left a residual odor of vinegar on the pulp after air drying. There was little residual odor from the air dried pulp after bleaching with peracetate oxidant and C102.

The increased bleaching efficiency observed for peracetate oxidant over peracetic acid is due to the efficient generation of useful reactive oxygen species in significant concentrations by the peracetate oxidant solution. It was previously demonstrated that the presence of hydrogen peroxide inhibits the bleaching activity of peracetate oxidant and peracetic acid solutions. Peracetate oxidant solution is formulated and produced in a way that makes it more active and superior as a bleaching agent over peracetic acid, particularly in pH neutral to alkaline conditions.

Raising the bleaching temperature to 90° C. and/or raising the bleaching pH to 11 had some positive effects on pulp brightness and bleaching rate. More significantly, conducting pulp bleaching with sequential doses, or charges, of peracetate oxidant at lower concentration was found to produce brighter pulp than a single charge of oxidant at a high concentration.

Example 4: TOX Formation Tests in Water

A flowback water sample was treated with peracetate oxidant solution, peracetic acid, chlorine bleach and a blank (no oxidant) at 22° C. with an excess oxidant dose concentration to provide an extended contact time between organic contaminants and elevated concentration of oxidant. The untreated water had a pH of 5.8, ORP of 135 mV vs SHE, 86 mg/L iron, turbidity of 300 FNU, an APB population of greater than 10 million cells/mL and a SRB population of greater than 10 million cells/mL. The water was a hazy tan color and had a mild hydrocarbon odor.

Four 1 L glass beakers were filled with 900 mL of flowback water and placed on a Phipps and Bird jar test apparatus. The pH of the water was adjusted slightly to pH 6.5 with 1 M NaOH and the oxidants were added to three of the jars while mixing all of them at 150 rpm for about 8 minutes. The jars were mixed at 25 rpm for another 112 minutes then mixing was stopped and the solids allowed to settle for about 60 minutes. The four water samples were decanted into amber glass bottles and preserved with sulfuric acid for total organic halide analyses, which were conducted by a third party laboratory.

TABLE 4

| Oxidant | Initial Concentration (mg/L) | TOX (mg/L) |
|---|---|---|
| Blank | 0 | BDL |
| Peracetate oxidant | 80 (as PAA) | BDL |
| Peracetic Acid | 80 (PAA), 112 ($H_2O_2$) | BDL |
| Chlorine Bleach | 80 | BDL |

BDL = below detection limit, less than 0.05 mg/L

Total organic halide was below detection limit in all cases indicating that TOX formation was not an issue for this flowback water sample under the treatment conditions.

Example 5: TOX Formation Tests in Pulp Bleaching

The potential of organic halide formation during pulp bleaching was compared between peracetate oxidant solution, peracetic acid and chlorine dioxide at 50° C. and 5% pulp consistency. The pulp slurries were prepared in distilled water containing 1.0% sodium chloride to simulate salt accumulation in a bleaching circuit, which can contribute to the formation of free chlorine and chlorinated byproducts in the presence of oxidizing bleaching chemicals. The pulp slurries were prepared by weighing out 45.0 g of 50 lb Kraft paper (Pacon Corp.), cutting the paper into smaller pieces (about 1 square inch), wetting the paper in 650-750 mL of distilled water containing 1.0% NaCl and pulping the mixture in a blender for about 2-3 minutes until the consistency was approximately uniform. The pulp slurry was put into a 1 L glass beaker in a heated water bath. The beakers were fitted with liquid-tight covers to minimize evaporative losses of water and oxidants. After the pulp slurry was heated the oxidant solution and additional salt water was added to make a final composition of about 855 g water, 45.0 g of air-dry pulp, 8.55 g NaCl and the oxidant. The oxidant was mixed into the pulp slurry thoroughly with a stainless steel spatula for several minutes and then mixed periodically throughout the 2 hour bleaching period. The pH of the slurry was left at the natural pH created by each oxidant in the presence of the pulp.

The amount of oxidant used in each test was enough to partially bleach the amount of lignin present so that the oxidant was the limiting reagent. When peracetate oxidant was combined with Kraft pulp the evolution of some gas was observed accompanied by rapid bleaching that was clearly visible within the first few minutes. Chlorine dioxide also bleached the pulp rapidly, but to a lesser extent because it was applied at a lower concentration due to its limited solubility and high volatility. Peracetic acid produced a large amount of gas, but was least effective at bleaching. After 2 hours at 50° C. the pulp slurries were vacuum filtered through a Buchner funnel over a medium porosity filter paper. There was no residual oxidant present in the filtrates. The four filtrate solutions recovered were put into amber glass bottles and preserved with sulfuric acid for total organic halide analyses, which were conducted by a third party laboratory.

Each of the filtrate water solutions had a different color. The filtrate from chlorine dioxide was the darkest orange, the peracetate oxidant filtrate was light yellow, the peracetic acid filtrate was pale yellow and the blank's filtrate was golden-yellow.

Peracetate oxidant formed the least amount of TOX under the bleaching conditions. Normalizing the TOX formation to the concentration of oxidant used, the peracetate oxidant formed about 2.7 times less TOX than peracetic acid and about 10.4 times less TOX than chlorine dioxide. The peracetate oxidant solution provides strong bleaching performance and greatly reduced organic halide oxidation byproduct formation potential compared to conventional bleaching agents. The peracetate oxidant can significantly reduce pollution caused by the formation of halogenated oxidation byproducts.

TABLE 5

| Oxidant | Initial Oxidant Concentration (mg/L) | TOX (mg/L) | Normalized TOX (mg/L per 1000 mg/L oxidant) |
|---|---|---|---|
| Blank | 0 | 0.68 | — |
| Peracetate oxidant | 4000 (as PAA equivalents) | 6.7 | 1.7 |
| Peracetic Acid | 4000 (PAA), 5400 ($H_2O_2$) | 17.8 | 4.5 |
| Chlorine Dioxide | 1000 | 17.7 | 17.7 |

Example 6: Analysis of Bromate Formation

Synthetic sea water was prepared by dissolving 71 grams of "Instant Ocean™" in 1000 mL of distilled water according to the product directions. A produced water sample was collected from an oil well site in northeast Colorado and contained about 31 mg/L iron, 50 mg/L magnesium, 210 mg/L calcium, 89 mg/L bromide, suspended solids (appeared tan, turbid) and microbes. Water samples were treated at room temperature (18-22° C.) using a programmable Phipps and Bird jar tester equipped with flat mixing blades and 1 L beakers. The water clarification test program consisted of a 1.25 minute rapid mix at 290 rpm impeller speed, and a slow mix at 25 rpm until 60 minutes had passed. The peracetate oxidant solution was added to 800 mL of water as a slug dose of 1.6% (wt/vol) solution at the beginning of the rapid mix. For the test that included clarification the additional water clarification chemicals were added during the rapid mix period.

Each jar test water sample was analyzed for bromide and bromate using EPA method 300.1. After treatment and contact time with the oxidant water samples were put into sealed containers and refrigerated until analysis (250 mL poly bottles for bromide samples and 250 mL amber glass bottles with 2 mL of ethylenediamine preservative for bromate samples). Analyses were conducted by a third party laboratory.

Solution pH was measured using a high sodium pH electrode (Oakton) with three point calibration. ORP was measured using a platinum electrode ORP probe (Oakton) calibrated with a ORP standard (420±3 mV vs SHE, Orion 967901, Thermo Fisher). A HACH DR 900 colorimeter and corresponding procedures with the appropriate HACH reagent kits were used to measure various water parameters (iron, calcium, magnesium) after diluting samples with an appropriate amount with distilled water. Iron analysis by HACH method 10249 was modified to avoid interferences from the produced water matrix (color indicator development time was increased). The peracetate oxidant concentration was measured using the HACH iodometric titration method for hydrogen peroxide.

Table 6 shows a summary of test results for this study. Treatment tests were modeled after that used in a recent study of disinfection byproducts formed in sea water when using commercial peracetic acid products. Treatment tests were conducted by adding 25 or 100 mg/L peracetate oxidant to 800 mL water samples and monitoring the pH and ORP during the first 60 minutes of contact time with the oxidant. The pH, maximum ORP (ORPmax), bromide and bromate concentrations are reported.

For seawater samples the ORP increased to a maximum value in about 45-55 minutes and remained at an elevated level for at least 18 hours. Seawater samples were allowed to stand at room temperature for about 18 hours to provide an extended contact time with the oxidant residual before preserving for analysis. For produced water samples, the maximum ORP was reached in about 2 minutes and decreased more rapidly afterwards due to contaminants reacting with the oxidant. The produced water sample treated with 25 mg/L peracetate oxidant solution fully consumed the oxidant within an hour. The last produced water sample treated with 100 mg/L peracetate oxidant solution and clarified was treated with the additional use of a coagulant and floc aid followed by solids separation by gravity settling to produce a water-clear solution with a reduction in pH to 7.6, iron to 3.5 mg/L and calcium to 180 mg/L. Produced water samples were allowed to stand at room temperature for about 6 hours to provide an extended contact time with the oxidant residual before preserving for analysis.

No bromate formation was detected in the treatment of the simulated seawater composition and production water from the oilfield under conditions that are favorable for bromate formation. In contrast, bromate formation as an oxidation byproduct is a well-known issue for oxidants such as ozone and peracetic acid.

TABLE 6

| Water Type | Treatment | pH | ORPmax (mV vs SHE) | Bromide (mg/L) | Bromate (mg/L) |
| --- | --- | --- | --- | --- | --- |
| Seawater | none | 8.1 | 412 | 116 | ND |
| Seawater | 25 mg/L peracetate oxidant | 8.1 | 903 | 136 | ND |
| Seawater | 100 mg/L peracetate oxidant | 8.2 | 930 | 119 | ND |
| Produced Water | none | 7.9 | 445 | 89.1 | ND |
| Produced Water | 25 mg/L peracetate oxidant | 8.2 | 639 | 79.0 | ND |
| Produced Water | 100 mg/L peracetate oxidant | 8.2 | 737 | 65.6 | ND |
| Produced Water | 100 mg/L peracetate oxidant with clarification | 7.5 after clarification | 769 | 77.3 | ND |

ND = non-detect

Example 7: ROS Production Rates in Water and in a Pulp Slurry at Elevated Temperature In this example the rate of ROS generation by the peracetate formulation is directly proportional to the rate of peracetate concentration decline. Measurement of peracetate concentration over time was conducted in clean tap water and in 5% consistency hardwood pulp at 70° C., which is a common temperature for pulp delignification and bleaching processes in a paper mill.

In a first test a 250 mL solution of tap water containing an initial peracetate concentration of 3000 mg/L at 70° C. was made by mixing 37.5 mL of a 2.0% wt/vol solution of the peracetate formulation concentrate (made at room temperature) into 212.5 mL of tap water already heated to 70° C. in a 1 L glass beaker in a hot water bath. Samples were removed for analysis at regular time intervals and the results presented in FIG. 3. The initial pH was 9.0 and the final pH was 5.8. The initial ORP was 540 mV vs SHE, which increased to a maximum of 785 mV in 30 minutes.

In a second test a 250 mL slurry of a north American hard wood pulp fiber (16.0 kappa number) at 5% consistency and 70° C. containing an initial peracetate concentration of 3000 mg/L was made by mixing 37.5 mL of a 2.0% wt/vol solution of the peracetate formulation concentrate (made at room temperature) into 200 mL of tap water with 12.5 g (oven dry weight) of pulp fiber already heated to 70° C. in a 1 L glass beaker in a hot water bath. The slurry was thoroughly mixed and samples of the oxidant liquor were removed and filtered for analysis at regular time intervals. The results are presented in FIG. 3. The initial pH was 8.8 and the final pH was 6.4. The initial ORP was 675 mV vs SHE, which increased to a maximum of 850 mV in 25 minutes.

The peracetate concentration decreased at a similar rate for both tests over the first 10-20 minutes. After about 20 minutes the residual peracetate concentration in tap water persisted longer at a higher concentration than the residual in the pulp slurry. At 30 minutes the peracetate residual in tap water was about 9.6% higher than the residual in the pulp slurry relative to the initial peracetate concentration.

Under the initial pH conditions in tap water, the peracetate anion (initially produced as the sodium peracetate salt) is in large excess of the acid form, but acidity in the water (e.g., bicarbonate, oxidant hydrolysis products) will convert a portion of the peracetate to the protonated, acid form. Plotting 1/[peracetate] in FIG. 5 shows an initial linear region up to about 20 minutes, which is consistent with second order reaction behavior dominating the kinetics of peracetate concentration decline. The slope of the linear fit is proportional to the reaction rate constant. After 20 minutes the rate of peracetate decline slows and departs from second order behavior, but then resumes again with second order behavior by 80 minutes at the same slope (rate constant) as initially measured.

The temporary departure from second order behavior suggests the buildup of ROS species or complexes that may interfere with the singlet oxygen forming reaction occurred until they dissipated or were consumed over nearly an hour. The buildup of ROS species can only occur if they persist in solution longer than just singlet oxygen, which has a lifetime of only several microseconds in water.

A longer-lived, high ORP combination of singlet oxygen, superoxide and other radical fragments caused by thermal or catalytic disproportionation of the parent oxidant has been described in FIG. 4 here. A one electron reduction of singlet oxygen can form superoxide in-situ. A buildup of these species in clean water during the initial rapid generation of ROS, where they are not consumed by reactive substrates or impurities, may disrupt the second-order bimolecular reaction. Once these longer lived ROS species are dissipated or consumed the second-order reaction can dominate the observed peracetate decline rates again.

The initial and final pH in the wood pulp mixture are similar to those in tap water. Plotting 1/[peracetate] in FIG. 6 shows an initial linear region up to about 20 minutes, which is consistent with second order reaction behavior dominating the initial kinetics of peracetate concentration decline. The linear slope (rate constant) in the 1/[peracetate] plots over the first 20-25 minutes is about 15% greater for pulp over clean tap water indicating that additional reactions of peracetate in the pulp environment are increasing the observed rate. After the first 20-25 minutes in the pulp sample the rate of peracetate decline follows a pseudo-first order behavior as shown by a linear relationship in the ln[peracetate] plot in FIG. 7. This behavior is dramatically different than that observed in clean tap water. In the pulp environment, the ROS will be consumed by reactions with lignin, hemicellulose, black liquor and other reactive materials or impurities present, thus not allowing ROS to build up significantly in the mixture. As the peracetate concentration decreases and the singlet oxygen reaction slows the rates of other peracetate-consuming reactions may compete making the peracetate decline appear to transition to a pseudo-first-order reaction behavior.

The above results indicate that nearly all of the peracetate is being consumed by reactions that evolve ROS or other reactions native to the peracetate. There is an unexpectedly small amount of peracetate (approximately 10% by concentration, 15% by rate constant) that may be consumed in the hardwood pulp by direct reactions with materials including black liquor carry-over, reactions catalyzed by metal impurities (e.g., Fe, Mn), and readily oxidized hydrocarbons.

The ROS, which are dominated by singlet oxygen generated by the peracetate formulation, are doing the majority of the delignification, brightening and bleaching reactions in pulp. Furthermore, the best ROS generation rate and concentration is within the first 10-15 minutes of applying the peracetate solution for pulp delignification under these test conditions and initial peracetate oxidant concentration.

Example 8: Kappa Number Reduction Vs Time and Peracetate Concentration

Further evidence supporting the conclusion in Example 7 is found in delignification experiments where the majority of kappa number reduction occurs in the first 5 minutes of reaction time. North American soft wood (pine) pulp fiber (kappa no. 35.42) and hard wood pulp fiber (kappa no. 16.00) were treated with the peracetate oxidant formulation at 5% pulp consistency and 65° C. and the natural pH of the pulp. The pulp slurries, or mixtures, were prepared by the same procedure as above and a 2.0% wt/vol peracetate solution was added in the appropriate amount to make the initial concentrations of 0.20% and 0.40%. The samples were contained ion 1 L glass beakers heated in a water bath.

Delignification was conducted for 5 minutes and 30 minutes to compare the extent of Kappa number reduction. Mixing was conducted by hand with a narrow spatula, intermittently over time. At the end of the reaction time period the oxidant residual was quenched by washing the pulp samples with 1.5 L of tap water through a screen lined with cheese cloth. A summary of test results is provided in Table 7.

Kappa numbers were measured in duplicate or triplicate using a micro-Kappa procedure that used 0.5 g of oven dried pulp fiber mass (¼-scale of the standard TAPPI T 236 om-99 method). Kappa number measurements were conducted on pulp samples stored damp after determining the percent solids of each sample.

The pH of pulp mixtures was measured with a high sodium pH electrode put directly into the pulp slurry. A thermocouple for temperature compensation of the pH reading was placed in the pulp during measurement.

TABLE 7

The two pairs of peracetate concentration conditions showed that 66% of the kappa number reduction occurred in the first 5 minutes of reaction time relative to the kappa reduction achieved in 30 minutes.

| PAc Conc. (%) | Reaction time (min) | Kappa no. | Kappa no. reduction | % Kappa reduction | Initial pH | Final pH |
|---|---|---|---|---|---|---|
| Control | — | 35.42 | — | — | 9.85 | |
| 0.20 | 5 | 31.38 | 4.04 | 11.4% | 9.84 | 8.92 |
| 0.20 | 30 | 29.28 | 6.14 | 17.3% | 9.86 | 7.24 |
| 0.40 | 5 | 27.66 | 7.76 | 21.9% | — | 8.41 |
| 0.40 | 30 | 23.58 | 11.84 | 33.4% | — | 6.94 |

Addition of the peracetate oxidant had little to no impact on the initial pH of the pulp mixture at its natural pH. The pH of the pulp mixtures decreased over time and the magnitude of pH reduction increased with increasing kappa reduction, reaction time and initial oxidant concentration. Other tests conducted with the initial pH of pulp mixtures adjusted with sodium hydroxide to pH 11.0-11.5 produced less kappa number reduction for a given set of conditions and higher final pH.

Conducting delignification tests at greater than about pH 10.5 did not improve delignification performance. At pH 11 and greater delignification of wood pulp was partially inhibited (kappa number reduction was less). According to the results in [Ref: Gerdes, R.; Wohrle, D.; Spiller, W.; Schneider, G.; Schnurpfeil, G.; Schulz-Ekloff, G.; Journal of Photochemistry and Photobiology A: Chemistry; 111 (1997) 65-74.] high pH enhances further breakdown of phenols resulting in increased oxygen consumption. Conducting delignification at less than pH 11 is more efficient for lignin extraction with the peracetate oxidant formulation, which may be a result of oxidative reactivity of phenols being moderated to slow further oxygen reactions with the lignin.

[00250] A direct observation of ongoing oxidation reactions with extracted lignin was slow bleaching of the color from spent peracetate oxidant liquors containing several hundred ppm of active oxidant residual. Over several hours the color was bleached to very pale hues. (i.e., yellow to orange-colored quinone-like oxidation byproducts being further oxidized to nearly colorless byproducts). Reactions of the peracetate oxidant with extracted lignin may compete or interfere with delignification of fiber as kappa number increases.

Example 9: Improving Delignification Performance with and Mixing Efficiency and Peracetate Oxidant Dose The energy and timing of mixing was tested to determine their impact on delignification efficiency. For these tests a 250 g pulp mixture was mixed vigorously with a wide plastic paddle for the entire reaction time or for just the first minute. The same preparations of softwood and hardwood pulps at 5% consistency were used as described in Example 8. A lower concentration of peracetate oxidant was used to examine the impact of different mixing methods over a ten minute period at 70° C. A summary of test results is provided in Table 8.

TABLE 8

| | Softwood Pulp | | | | |
|---|---|---|---|---|---|
| PAc Conc. (%) | Total Reaction time (min) | Rapid Mix Time (min) | Kappa no. | Kappa no. reduction | % Kappa reduction |
| Control | — | — | 35.42 | — | — |
| 0.18 | 10 | 10 | 22.43 | 12.99 | 36.7% |
| 0.18 | 10 | 1 | 24.43 | 10.99 | 31.0% |
| 0.09 + 0.09 | 10 | 5 + 5 | 25.82 | 9.60 | 27.1% |
| 0.08 + 0.16 | 10 | 5 + 5 | 26.69 | 8.73 | 24.6% |

Vigorous mixing of the softwood pulp for 10 minutes with 1800 ppm initial oxidant dose produced a 36.7% kappa reduction. Limiting the mixing to just the first minute decreased the kappa reduction to 31.0%. Conducting the test with a first oxidant dose of 900 ppm and mixing for 5 minutes then adding another 900 ppm oxidant dose and mixing for another 5 minutes produced a 27.1% kappa reduction.

Repeating the above two-step addition of oxidant for the softwood with 800 and 1600 ppm doses produced a 24.6% kappa reduction. The 1600 ppm dose was added at 5 minutes on top of a 285 ppm measured residual for a combined maximum concentration of 1885 ppm. For the softwood pulp the kappa reduction was greatest with the highest initial concentration of oxidant with only a single reaction step. The higher oxidant demand corresponding with the higher initial kappa number may be caused by greater lignin concentration and/or reactivity of extractible materials in the softwood black liquor. The observed oxidant demand of extracted materials appears to reduce the concentration of singlet oxygen available to react with the pulp, especially when a partial extraction is done prior to the second oxidant dose in the softwood two-step experiments (the final oxidant concentration was 760 mg/L). The same tests were conducted on the hardwood pulp and the results shown in Table 9.

TABLE 9

| | Hardwood Pulp | | | | |
|---|---|---|---|---|---|
| PAc Conc. (%) | Total Reaction time (min) | Rapid Mix Time (min) | Kappa no. | Kappa no. reduction | % Kappa reduction |
| Control | — | — | 16.00 | — | — |
| 0.18 | 10 | 10 | 11.37 | 4.63 | 28.9% |
| 0.18 | 10 | 1 | 12.71 | 3.29 | 20.6% |
| 0.09 + 0.09 | 10 | 5 + 5 | 10.90 | 5.10 | 31.9% |
| 0.08 + 0.16 | 10 | 5 + 5 | 9.77 | 6.23 | 38.9% |

Vigorous mixing of the hardwood pulp for 10 minutes with 1800 ppm initial oxidant dose produced a 28.9% kappa reduction. Reducing the mixing to just the first minute decreased the kappa reduction to 20.6%. Conducting the test with a first oxidant dose of 900 ppm and mixing for 5 minutes then adding another 900 ppm oxidant dose and mixing for another 5 minutes produced a 31.9% kappa reduction.

Repeating the above two-step addition of oxidant for the hardwood with 800 and 1600 ppm doses produced a 38.9% kappa reduction. The 1600 ppm dose was added at 5 minutes on top of a 285 ppm measured residual for a combined maximum concentration of 1885 ppm. For the hardwood pulp the kappa reduction was greatest for the two-step process with the highest second dose concentration. The lower overall oxidant demand corresponding with the lower initial kappa number may not be significantly limiting the concentration of singlet oxygen available to react with the pulp in the hardwood two-step experiments (the final oxidant concentration was 1000 mg/L).

Delignification of pulps with low to medium kappa (i.e., initial kappa numbers of 12-20) benefits significantly from two-step oxidation processes. Delignification of pulps with medium kappa (i.e., initial kappa numbers of 20-40) is expected to benefit from a two-step delignification process, but removal of the black liquor (oxidant liquor) after the first step may be required. This oxidant liquor still contains active oxidant and can be used in an initial wash step of brownstock.

Example 10: Counter-Flow Delignification Process

A counter-flow delignification process was designed to reduce consumption of the peracetate oxidant formulation The counter-flow use of the peracetate oxidant is described for FIG. 8 for processing 1000 tons (short tons) per day of oven dry (o.d.) hardwood pulp with an initial kappa number of 14.2 and a target final kappa number of 7.5 or less. The 15% consistency brownstock was passing through the process at a rate of 9253 lbs/min. A 5.0% peracetate solution (accounted for as peracetate ion) was added to the pulp stream at injection point A at a rate of 45.2 gpm (389 lb/min of 5% solution or 28 lb peracetate per o.d. ton). The initial peracetate concentration in the pulp was 2020 ppm and the pulp was diluted to 14.4% consistency. The residence time or oxidation time in the second pulp chest was 7 minutes. The concentration of peracetate decreased to about 1000 ppm.

The pulp was washed with 100 gpm of clean water added at injection point B. The wash liquor was collected in the third black liquor tank at a rate of 145 gpm and contained about 310 ppm peracetate residual. The wash liquor was transferred to the first wash stage at a rate of 145 gpm where it was added at injection point C. A wash liquor transfer line to the second wash stage was not used during this operation.

The wash liquor diluted the pulp from the first wash stage to 13.3% consistency and contained an initial oxidant concentration of 36 ppm (about 0.7 lb peracetate per ton o.d. pulp). The oxidant was fully consumed within the 3-minute residence time in the first fiber chest. Optionally, a second peracetate solution addition (not shown) could be made at injection point C with the wash liquor to increase the peracetate concentration to several hundred ppm for increased oxidation in the first fiber chest and oxidant carry-over to the second wash stage.

The pulp was dewatered to remove the black liquor in the second wash stage, before addition of fresh peracetate solution. The black liquor was collected in the second black liquor tank at a rate of 145 gpm. The black liquor in the second black liquor tank was transferred to the outlet of the first black liquor tank D at a rate of 145 gpm. From this point the black liquor was directed to injection point E at the dilution mixer or directed to the black liquor removal point F. The diluted brownstock was dewatered at the first wash stage and the black liquor is collected in the first black liquor tank. The black liquor was cycled back into the dilution mixer or directed to the black liquor removal point F. The black liquor at this point may contain 15% dissolved and suspended solids and is sent to a recovery boiler or is collected for further processing (i.e., sell the black liquor or produce lignin and reuse the water).

Within the described process there may be additional pulp process stages, such as a fiber screening stage or additional washing stages. The first fiber chest may also be omitted. The general process approach remains the same despite variations in the specific number and type of process steps in a given facility.

Example 11: Medium Consistency Delignification Performance

Delignification tests were conducted on north American hardwood pulp (after sulfide digestion with initial Kappa number 16.0) at 12% and 15% pulp consistency at 70° C. with the peracetate oxidant formulation. Delignification is often conducted in a pulp mill at medium pulp consistency, typically between about 10% to 18% oven dried (o.d.) fiber by weight.

Conducting medium and high consistency tests on a small scale is challenging because mixing methods are often inefficient, non-uniform and low energy. A mixing apparatus was constructed to efficiently mix high consistency pulp. The mixing apparatus consisted of a jacketed stainless steel beaker, at least 2 L volume, fastened to a variable speed rotating table. A variable speed overhead mixer was positioned over the jacketed beaker to turn a stainless steel shaft outfitted with multiple stainless steel impeller blades having a diameter of at least half the inside diameter of the beaker. The impeller was positioned off center from the beaker's rotational axis to allow its blades to sweep within ⅛ inch of the side of the beaker and to within ¼ inch of the bottom of the beaker. The beaker and impeller were rotated in opposite directions relative to one another to provide thorough mixing of high consistency pulp mixtures.

Pulp mixtures were diluted to their target consistency with tap water minus the volume or mass of oxidant to be added. The diluted pulp was heated to 70-75° C. in a Pyrex beaker with a microwave oven. The jacket of the stainless steel beaker of the mixer was filled with hot water, greater than 70° C. The heated pulp was transferred to the hot, jacketed beaker of the mixer. The mixing apparatus was operated continuously during the delignification test period. The temperature of the pulp was maintained at 65-72° C. for the duration of the mixing process.

A 4.55% peracetate oxidant solution (measured as peracetate ion) was produced by a peracetate oxidant generation system similar to that described in U.S. patent application Ser. No. 14/020,828. Freshly made oxidant solution was added in a slug dose to the mixing pulp to provide specified initial oxidant concentrations as ppm on a mass of oxidant to total mass pulp slurry basis. After a specific period of mixing time with oxidant the pulp was removed from the mixer, partially drained of black liquor using a vacuum filter (Buchner funnel with medium filter paper) and washed with tap water. The oxidant residual in the first black liquor drained was measured by iodometric titration.

Results of the tests are summarized in Table 10. Each test sample consisted of 103 g of o.d. pulp diluted in liquid (by weight) to the treatment consistency. The liquid consisted of the black liquor carryover in the original wet pulp sample (25.8% consistency), the oxidant solution mass and tap water making up the balance.

The first two tests were conducted with a single oxidation step at a nominal temperature of 70° C. for 5 minutes followed by washing with 1.5 L of tap water (after a sample of black liquor was collected for analysis). The black liquor filtrate was a light amber, yellow-tan color.

The third test was conducted in the same manner as the second except the reaction with oxidant was done in two steps. In the first step, 3a, a lower dose of oxidant was applied (600 ppm), which was fully consumed within about 1.5 minutes. This sample was washed with about 0.5 L of tap water providing a dark amber, black liquor filtrate. A filtrate volume was recovered from the pulp that was equal to the amount of wash water plus the amount of oxidant solution to be added in the second step to maintain 15% consistency. The sample was re-heated to 70° C. and treated a second time in test 3b with a higher concentration of oxidant (1700 ppm) and reacted for five minutes before washing. The black liquor filtrate from the second step was a pale yellow color.

TABLE 10

Delignification test summary.

| Test no. | Treatment Consistency (%) | Initial Peracetate Conc. (ppm) | Pulp Mass, (o.d. g) | Peracetate Solution Mass (g) | Total Pulp Slurry Mass (g) | Kappa no. Reduction | Residual Peracetate in Liquor (mg/L) |
|---|---|---|---|---|---|---|---|
| 1 | 12 | 2000 | 103 | 37.9 | 862 | 3.5 | ≥190 |
| 2 | 15 | 2300 | 103 | 34.8 | 689 | 4.3 | 190 |
| 3a | 15 | 600 | 103 | 9.1 | 689 | — | 0 |
| 3b | 15 | 1700 | 103 | 25.8 | 689 | 5.3 | 856 |

The reduction in kappa number was greatest for the two-step treatment with peracetate oxidant. A very rapid removal of the most reactive fraction of lignin and other materials occurred in the first oxidation step, 3a, using a lower oxidant dose. The first oxidation step allowed the more reactive and oxidant-consuming materials to be removed in the black liquor before the second oxidation step, 3b, which provided more efficient oxidant use as shown by the largest kappa reduction and highest oxidant residual in the recovered liquor prior to washing.

These results demonstrate that the peracetate oxidant formulation is effective for delignification at medium pulp consistency. Performance increased with increasing treatment consistency, which corresponds with less dilution of the oxidant in the liquid phase of the pulp slurry.

These results show that a two-step delignification process provides a method to increase delignification efficiency at medium pulp consistency when using the peracetate oxidant formulation. The amount of peracetate oxidant used may be reduced with a two-step delignification process. Alternatively, the amount of oxidant carryover may be increased with a two-step delignification process thereby providing longer oxidation times in a forward-flow or counter-flow process to achieve greater delignification, greater kappa number reduction and increased brightening.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of treating pulp in a delignification process, the delignification process comprising:

adding a parent oxidant solution to a pulp at a primary addition point and after the adding, mixing a mixture with the pulp with the added parent oxidant solution; and the parent oxidant solution being a peracetate oxidant solution to generate a reactive oxygen species in the resulting mixture, wherein the peracetate oxidant solution has properties as added to the pulp, wherein the properties comprise:

a pH in a range of from pH 10 to pH 12;

peracetate anions and a peracid with a molar ratio of peracetate anions to peracid of from 60:1 to 6000:1; and either no hydrogen peroxide or hydrogen peroxide wherein a peracetate anion to hydrogen peroxide molar ratio is greater than 16:1; and wherein after a period of time following the adding, separating from the pulp an oxidant liquor containing residual active peracetate oxidant and conveying the oxidant liquor to a secondary addition point, upstream of the primary addition point, where the pulp at a temperature of from 50° C. to 95° C. and a pH of from pH 9 to pH 11 and the oxidant liquor are contacted and mixed and disproportionation of the residual active peracetate oxidant of the oxidant liquor to reactive oxygen species is catalyzed by impurities in the pulp at the secondary addition point, and wherein oxidant demand of the pulp is reduced downstream of the second addition point by the time the pulp reaches the primary addition point.

2. The method of claim 1, wherein the pulp is at a temperature in a range of from 50° C. to 95° C. during the adding and mixing.

3. The method of claim 1, further comprising, after the delignification process, bleaching the pulp with a bleaching sequence in which the pulp is bleached with chlorine dioxide, the bleaching sequence comprising D(EOP)DD, except not including at least one said D; and wherein each said D is a treatment stage with chlorine dioxide and the EOP is a treatment stage of oxidative extraction with alkaline hydrogen peroxide.

4. The method of claim 1, wherein the pulp is not subjected to chlorine dioxide treatment following the contacting with the peracetate oxidant solution.

5. The method of claim 1, comprising a pulping operation prior to the delignification process and a bleaching operation following the delignification process, and wherein the method is a totally chlorine free pulp treatment process.

6. The method claim 1, wherein the method is in the absence of oxygen delignification of the pulp.

7. The method of claim 1, wherein the delignification process comprises oxygen delignification prior to the adding the parent oxidant solution to the pulp.

8. The method of claim 1, wherein the delignification process comprises oxygen delignification following the adding the parent oxidant solution to the pulp.

9. The method of claim 1, wherein the pulp is maintained at a pulp consistency during the adding and the mixing in a range of from 10% to 20% oven dried fiber by weight.

10. The method of claim 1, wherein the primary chemical species for delignification during the mixing is singlet oxygen generated in the mixture by the peracetate oxidant solution following the adding.

11. A method of treating pulp, comprising:
feeding a source of a pulp in a forward-flow direction to a delignification process, and wherein the delignification process comprises:
dewatering the pulp in a first wash stage, including separating first black liquor from the pulp;
after the first wash stage, providing the pulp to a first fiber chest;
after a residence time in the first fiber chest, subjecting the pulp to a second wash stage where the pulp is dewatered, and including separating second black liquor from the pulp;
after the second wash stage providing the pulp to a second fiber chest;
after a residence time in the second fiber chest, subjecting the pulp to a third wash stage where the pulp is washed with clean water and dewatered, and including separating third black liquor from the pulp;
adding a parent oxidant solution to the pulp at a primary addition point and after the adding, mixing a mixture with the pulp with the added parent oxidant solution; and
the parent oxidant solution being a peracetate oxidant solution to generate a reactive oxygen species in the resulting mixture, wherein the peracetate oxidant solution has properties as added to the pulp, wherein the properties comprise:
a pH in a range of from pH 10 to pH 12;
peracetate anions and a peracid with a molar ratio of peracetate anions to peracid of from 60:1 to 6000:1; and
either no hydrogen peroxide or hydrogen peroxide wherein a peracetate anion to hydrogen peroxide molar ratio is greater than 16:1; and
wherein after a period of time following the adding, separating from the pulp an oxidant liquor containing residual active oxidant and conveying the oxidant liquor to a secondary addition point, upstream of the primary addition point, where the pulp and the oxidant liquor are contacted and mixed;
and wherein:
the primary addition point is in the second washing stage; and
the oxidant liquor comprises at least a portion of the third black liquor and the secondary addition point is in the first washing stage.

12. The method of claim 11, wherein the oxidant liquor comprises a first portion of the third black liquor and the peracetate oxidant solution comprises a second portion of the third black liquor.

13. A method treating pulp, comprising:
a delignification process, the delignification process comprising:
adding a parent oxidant solution to a pulp at a primary addition point and after the adding, mixing a mixture with the pulp with the added parent oxidant solution; and
the parent oxidant solution being a first peracetate oxidant solution to generate a reactive oxygen species in the resulting mixture, wherein the first peracetate oxidant solution has first properties as added to the pulp, wherein the first properties comprise:
a pH in a range of from pH 10 to pH 12;
peracetate anions and a peracid with a molar ratio of peracetate anions to peracid of from 60:1 to 6000:1; and
either no hydrogen peroxide or hydrogen peroxide wherein a peracetate anion to hydrogen peroxide molar ratio is greater than 16:1; and
wherein after a period of time following the adding, separating from the pulp an oxidant liquor containing residual active oxidant and conveying the oxidant liquor to a secondary addition point, upstream of the primary addition point, where the pulp and the oxidant liquor are contacted and mixed;
bleaching the pulp with chlorine dioxide treatment after the delignification process, wherein the bleaching comprises a bleaching sequence of $D_0(PxO1)D_1D_2$, except not including at least one of $D_1$ and $D_2$; and wherein the PxO1 is a bleaching stage comprising treatment of the pulp with a second peracetate oxidant solution having second properties when added to the pulp during the bleaching stage, wherein the second properties comprise:
a pH in a range of from pH 10 to pH 12;
peracetate anions and a peracid with a molar ratio of peracetate anions to peracid of from 60:1 to 6000:1; and
either no hydrogen peroxide or hydrogen peroxide wherein a peracetate anion to hydrogen peroxide molar ratio is greater than 16:1; and
wherein each said D is a treatment stage with chlorine dioxide and the PxO1 is a treatment stage of oxidative extraction with alkaline hydrogen peroxide.

* * * * *